United States Patent
Shaw et al.

(10) Patent No.: US 7,820,970 B1
(45) Date of Patent: Oct. 26, 2010

(54) FABRICATION OF THERMAL MICROPHOTONIC SENSORS AND SENSOR ARRAYS

(75) Inventors: Michael J. Shaw, Tijeras, NM (US); Michael R. Watts, Albuquerque, NM (US); Gregory N. Nielson, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 12/491,596

(22) Filed: Jun. 25, 2009

Related U.S. Application Data

(63) Continuation-in-part of application No. 11/950,821, filed on Dec. 5, 2007, now Pat. No. 7,667,200.

(51) Int. Cl.
*G01J 5/00* (2006.01)
(52) U.S. Cl. .................................. 250/338.1
(58) Field of Classification Search .... 250/338.1–338.5
See application file for complete search history.

(56) References Cited

U.S. PATENT DOCUMENTS

| | | | | |
|---|---|---|---|---|
| 6,489,615 | B2* | 12/2002 | Bluzer | 250/338.1 |
| 6,777,244 | B2* | 8/2004 | Pepper et al. | 436/165 |
| 6,888,973 | B2* | 5/2005 | Kolodziejski et al. | 385/14 |
| 2003/0052271 | A1* | 3/2003 | Fedder et al. | 250/338.4 |
| 2006/0091284 | A1* | 5/2006 | Viens et al. | 250/201.9 |
| 2007/0110358 | A1* | 5/2007 | Hu et al. | 385/14 |

OTHER PUBLICATIONS

John R. Vig et al, "Microresonator Sensor Arrays", 1995 IEEE International Frequency Control Symposium, May 31-Jun. 2, 1995, San Francisco, CA, pp. 852-869.
John R. Vig et al, "Uncoiled IR Imaging Array Based on Quartz Microresonators", Journal of Microelectromechanical Systems, vol. 5, No. 2, 1996, pp. 131-137.
Yoonkee Kim et al, "Experimental Results on a Quartz Microresonator IR Sensor", 1997 IEEE Ultrasonics Symposium, Oct. 5-8, 1997, Ontario, Canada, 1997, pp. 449-453.
Tomohiro Ishikawa et al, "Performance of 320×240 Uncolled IRFPA with SOI Diode Detectors", Proceedings of SPIE, vol. 4130 (2000), pp. 152-159.
P. Neuzil et al, "Evaluation of thermal parameters of bolometer devices", Applied Physics Letters, vol. 80, No. 10, 2002, pp. 1838-1840.

(Continued)

*Primary Examiner*—David P Porta
*Assistant Examiner*—Kiho Kim
(74) *Attorney, Agent, or Firm*—John P. Hohimer

(57) ABSTRACT

A thermal microphotonic sensor is fabricated on a silicon substrate by etching an opening and a trench into the substrate, and then filling in the opening and trench with silicon oxide which can be deposited or formed by thermally oxidizing a portion of the silicon substrate surrounding the opening and trench. The silicon oxide forms a support post for an optical resonator which is subsequently formed from a layer of silicon nitride, and also forms a base for an optical waveguide formed from the silicon nitride layer. Part of the silicon substrate can be selectively etched away to elevate the waveguide and resonator. The thermal microphotonic sensor, which is useful to detect infrared radiation via a change in the evanescent coupling of light between the waveguide and resonator, can be formed as a single device or as an array.

20 Claims, 23 Drawing Sheets

OTHER PUBLICATIONS

Pavel Neuzil et al, "Micromachined Bolometer With Single-Crystal Silicon Diode as Temperature Sensor", IEEE Electron Device Letters., vol. 26, No. 5, 2005, pp. 320-322.

D. K. Armani et al, "Ultra-high-Q toroid microcavity on a chip", Letters to Nature, vol. 421, Feb. 27, 2003, pp. 925-928.

Michael J. Shaw et al, "Fabrication techniques for low loss silicon nitride waveguides", Proceedings of SPIE Bellingham,WA, vol. 5720, 2005, pp. 109-118.

Junpeng Guo et al, "High-Q microring resonator for biochemical sensors", Proceedings of SPIE Bellingham,WA, vol. 5728, 2005, pp. 83-92.

Michael R. Watts et al, "Thermal Microphotonic Focal Plane Array (TM-FPA) for Uncooled High Sensitivity thermal Imaging", Paper presented at IEEE Conference on Lasers and Electro-Optics (CLEO 2007), Baltimore, MD, May 6-11, 2007.

Michael R. Watts et al, "Optical Resonators—Microphotonic Thermal Imaging", Nature Publishing Group, 2007.

* cited by examiner

FABRICATION OF THERMAL MICROPHOTONIC SENSORS AND SENSOR ARRAYS

CROSS REFERENCE TO RELATED APPLICATIONS

This is a continuation-in-part of application Ser. No. 11/950,821, filed Dec. 5, 2007 now U.S. Pat. No. 7,667,200.

GOVERNMENT RIGHTS

This invention was made with Government support under Contract No. DE-AC04-94AL85000 awarded by the U.S. Department of Energy. The Government has certain rights in the invention.

FIELD OF THE INVENTION

The present invention relates in general to sensing of infrared radiation, and in particular to methods for fabricating a thermal microphotonic sensor which senses infrared radiation by using heat produced by the infrared radiation to change a coupling of light between an optical waveguide and an optical resonator. The thermal microphotonic sensor can be formed as an individual sensor, or as a sensor array which is useful for infrared imaging applications.

BACKGROUND OF THE INVENTION

Infrared imaging is useful for detecting electromagnetic radiation at wavelengths beyond that which is visible to the human eye. Infrared imaging has applications for detecting people and/or machines by their emitted heat which is a form of infrared radiation. Such infrared imaging can be performed at night or when clouds or smoke would otherwise obscure normal vision. Infrared imaging is also important to provide detailed thermal images from space, or from a high altitude using an airplane or an unmanned aerial vehicle (UAV).

Many different types of infrared sensors are known in the art including bolometers and quantum detectors. Quantum detectors such as mercury cadmium telluride (MCT) detectors are highly sensitive but require cooling down to cryogenic temperatures. The cooling of MCT detectors consumes considerable electrical power and typically requires a cryostat. For satellite and UAV applications, the power consumption and weight of cryogenically-cooled quantum detectors can be limiting factors which prevent a scaling of quantum detectors to larger sizes.

Over the past decade, resistive bolometers have made significant inroads in room-temperature infrared imaging. However, in order to achieve a sufficient level of sensitivity, the resistive bolometers need to operate over an entire range of 7-14 μm where the blackbody emission peak lies at room temperature. Additionally, resistive bolometers do not enable sufficient standoff for many remote infrared sensing applications. Resistive bolometer array sizes currently remain below one megapixel which significantly limits resolution and the field of view for these devices.

What is needed is an infrared sensor and infrared sensor array that operates without cryogenic cooling and which provides a sensitivity higher than that of current resistive bolometers and preferably approaching or even exceeding that of conventional quantum detectors.

The present invention addresses this need by providing methods for fabricating thermal microphotonic sensors and sensor arrays which utilize heat provided by incident infrared radiation to change a coupling of light between one or more optical waveguides and optical resonators in the sensors and sensor arrays. Operation of the thermal microphotonic sensors and sensor arrays of the present invention can theoretically be more sensitive than other available types of uncooled detectors including resistive bolometers These and other advantages of the present invention will become evident to those skilled in the art.

SUMMARY OF THE INVENTION

The present invention relates to a method for fabricating a thermal microphotonic sensor for detecting infrared radiation. The method comprises the steps of: providing a silicon substrate; etching at least one opening and at least one trench in the silicon substrate to a first etch depth, with each opening being located where a support post for an optical resonator will be subsequently formed, and with each trench being located where a base for an optical waveguide will be subsequently formed; filling in each opening and each trench with silicon oxide; depositing a layer of silicon nitride over the silicon substrate, and patterning the layer of silicon nitride to form each optical resonator and each optical waveguide; and etching the silicon substrate beneath each optical resonator and beneath each optical waveguide to a second etch depth which is less than or equal to the first etch depth, thereby elevating each optical resonator and each optical waveguide above the silicon substrate, with each optical resonator being elevated upon the support post, and with each optical waveguide being elevated upon the base which is located therebeneath. The step of etching each opening and trench in the silicon substrate can comprise a reactive ion etching (RIE) step.

The step of filling in each opening and each trench with silicon oxide can comprise thermally oxidizing portions of the silicon substrate surrounding each opening and each trench and thereby converting these portions of the silicon substrate into the silicon oxide which expands to fill in each opening and each trench. The method can include a chemical-mechanical polishing (CMP) step for removing any of the silicon oxide which expands above each opening and each trench prior to the step of depositing the layer of silicon nitride over the silicon substrate.

The step of depositing the layer of silicon nitride over the silicon substrate can comprise depositing the silicon nitride layer by chemical vapor deposition. The silicon nitride layer can be, for example, 0.2 to 0.3 microns (μm) thick. A CMP step can be used to planarize the silicon nitride layer and/or to adjust the thickness of the silicon nitride layer. This can be done prior to patterning the silicon nitride layer to form each optical resonator and each optical waveguide. Patterning the silicon nitride layer can be performed by masking the silicon nitride layer using a photolithographically-defined etch mask (e.g. comprising a photoresist) and then reactive ion etching portions of the silicon nitride layer which are not protected from etching by the etch mask. The step of patterning the silicon nitride layer can also form a plurality of tethers to connect each optical resonator to the support post for that optical resonator.

In some embodiments of the present invention, an infrared-absorbing coating can be deposited on each optical resonator. In other embodiments of the present invention, an infrared-absorbing plate can be provided on the optical resonator and thermally coupled thereto by a plurality of legs which attach the infrared-absorbing plate to the optical resonator. This can be done by depositing a layer of polycrystalline silicon over the silicon substrate after the step of patterning the layer of silicon nitride; etching the layer of polycrystalline silicon to provide a plurality of openings down to the optical resonator at locations where the plurality of legs will be subsequently formed; depositing another layer of silicon nitride over the layer of polycrystalline silicon and in the plurality of openings down to the optical resonator, with the layer of silicon nitride in the plurality of openings forming the plurality of legs; patterning the layer of silicon nitride over the layer of polycrystalline silicon and thereby forming the infrared-absorbing plate which is thermally coupled to the optical resonator by the plurality of legs; and etching away the layer of polycrystalline silicon prior to the step of etching the silicon substrate.

The step of etching the silicon substrate can comprise etching the silicon substrate with a selective etchant which etches the silicon substrate to the second etch depth without substantially chemically attacking the silicon oxide or the layer of silicon nitride. The selective etchant can comprise, for example, potassium hydroxide (KOH), ethylene diamine-pyrocatechol (EDP), tetramethyl ammonium hydroxide (TMAH) or xenon difluoride ($XeF_2$).

The present invention also relates to a method for fabricating a thermal microphotonic sensor for detecting infrared radiation which comprises the steps of: providing a silicon substrate; etching at least one opening and at least one trench in the silicon substrate to a first etch depth, with each opening being located where a support post for an optical resonator will be subsequently formed, and with each trench being located where a base for an optical waveguide will be subsequently formed; filling in each opening and each trench with silicon oxide which is formed from the silicon substrate by thermally oxidizing portions of the silicon substrate surrounding each opening and each trench; chemically-mechanically polishing the silicon substrate and thereby removing any of the silicon oxide which extends above the silicon substrate; depositing a layer of silicon nitride over the silicon substrate; reactive ion etching the layer of silicon nitride to form each optical resonator and each optical waveguide; and selectively etching the silicon substrate down to a second etch depth which is less than or equal to the first etch depth and thereby elevating each optical resonator and each optical waveguide above the silicon substrate.

The step of reactive ion etching the layer of silicon nitride can also form a plurality of tethers to connect each optical resonator to the support post for that optical resonator. A CMP step can also be used to polish the silicon nitride layer prior to reactive ion etching the silicon nitride layer.

The step of selectively etching the silicon substrate comprises selectively etching the silicon substrate using a selective etchant selected from the group consisting of KOH, EDP, TMAH and $XeF_2$.

In certain embodiments of the present invention, an infrared-absorbing coating can be deposited on each optical resonator. In other embodiments of the present invention, an infrared-absorbing plate can be provided on each optical resonator, with the infrared-absorbing plate being thermally coupled through a plurality of legs to the optical resonator. The infrared-absorbing plate and the plurality of legs which attach the infrared-absorbing plate to each optical resonator can be formed by depositing a layer of polycrystalline silicon over the silicon substrate after the step of reactive ion etching the silicon nitride layer to form each optical resonator and each optical waveguide; reactive ion etching the layer of polycrystalline silicon to provide a plurality of openings down to the optical resonator at locations where the plurality of legs will be subsequently formed; depositing another layer of silicon nitride on the layer of polycrystalline silicon and in the plurality of openings down to the optical resonator, with the layer of silicon nitride in the plurality of openings forming the plurality of legs; reactive ion etching the layer of silicon nitride on the layer of polycrystalline silicon and thereby forming the infrared-absorbing plate; and selectively etching away the layer of polycrystalline silicon prior to the step of selectively etching the silicon substrate.

Additional advantages and novel features of the invention will become apparent to those skilled in the art upon examination of the following detailed description thereof when considered in conjunction with the accompanying drawings. The advantages of the invention can be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings.

DETAILED DESCRIPTION OF THE INVENTION

Figure 1:
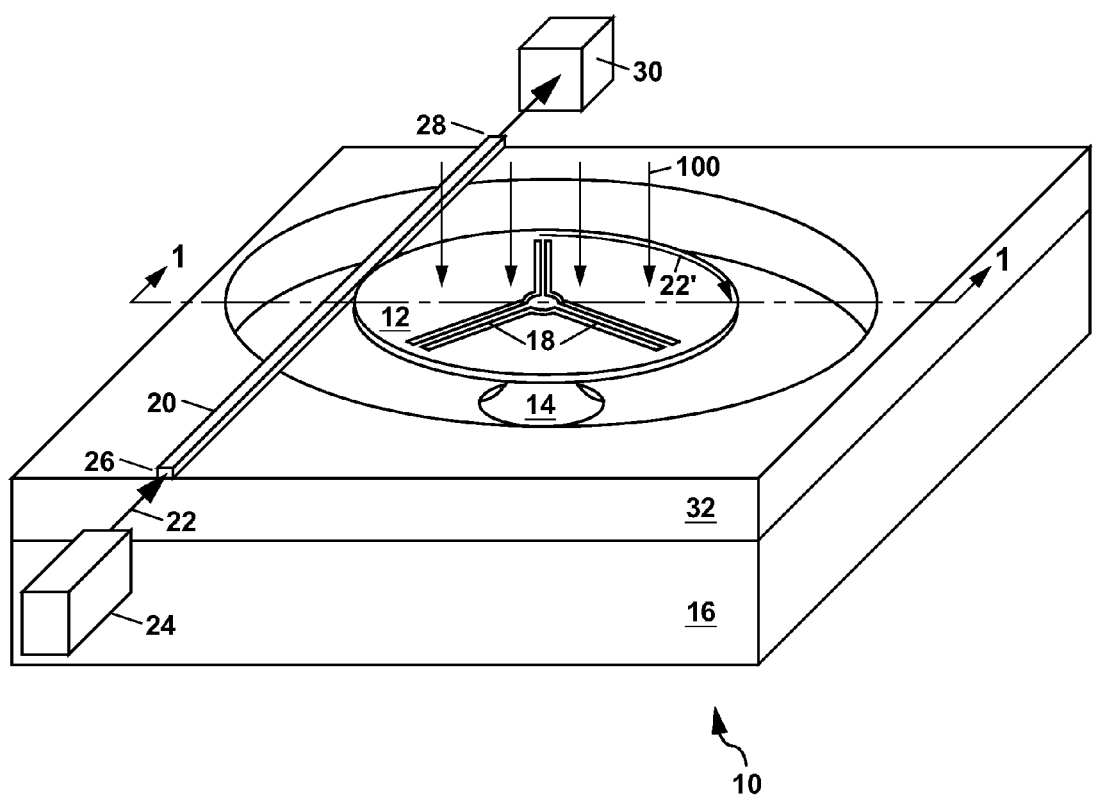
FIG. 1 shows a schematic perspective view of a first example of a thermal microphotonic sensor according to the present invention.

Referring to FIG. 1, there is shown a schematic perspective view of a first example of a thermal microphotonic sensor 10 of the present invention. The apparatus 10 comprises an optical resonator 12 (also referred to as an optical cavity, a microcavity, or a microring resonator). The optical resonator 12 is suspended on a support post 14 above a substrate 16 by a plurality of tethers 18 which are connected between the optical resonator 12 and the support post 14. An optical waveguide 20 is located near a periphery of the optical resonator 12 to allow an evanescent coupling of light 22 between the optical waveguide 20 and the optical resonator 12. Evanescent coupling between the optical waveguide 20 and the optical resonator 12 can occur when an air gap between the waveguide 20 and the resonator 12 has a spacing of less than or equal to the wavelength of the light 22.

The light 22 can be provided by a laser 24 which can be, for example, a single-frequency semiconductor laser such as a distributed Bragg reflector (DBR) laser operating at a wavelength of about 1.5 microns (μm). The light 22 from the laser 24 can be coupled into the optical waveguide 20 at an input end 26 thereof and is transmitted through the optical waveguide 20 to an output end 28 of the waveguide 20 where the light 22 is detected by a photodetector 30. The light 22 can be coupled into and out of the optical waveguide 20 using lenses and/or optical fibers which are not shown in FIG. 1.

In the example of FIG. 1, the light 22 in the optical waveguide 20 will be evanescently coupled into the optical resonator 12 when a frequency $f_L$ of the light 22, which is inversely proportional to the wavelength of the light 22, is near a resonant frequency $f_0$ of the optical resonator 12. The optical resonator 12 in the example of FIG. 1 is a ring resonator (also termed a microring resonator) in which a portion 22' of the light 22 which is evanescently coupled into the resonator 12 circulates around the periphery of the resonator 12 as illustrated by the curved arrow in FIG. 1 by being either waveguided or by reflecting off an outside edge of the resonator 12 in a whispering-gallery mode. The term "ring resonator" as used herein is intended to include optical resonators having a circular shape as shown in the example of FIG. 1 or having a polygonal shape (e.g. a square or rectangular shape), an elliptical shape, or oval shape (also termed a racetrack shape). Those skilled in the art will further understand that, although the portion 22' is shown as circulating in a clockwise direction, the portion 22' can circulate in a counterclockwise direction if the optical waveguide 20 were to be located on an opposite side of the resonator, or if the light 22 in the waveguide 20 were to propagate in an opposite direction to that shown in FIG. 1.

Figure 2:
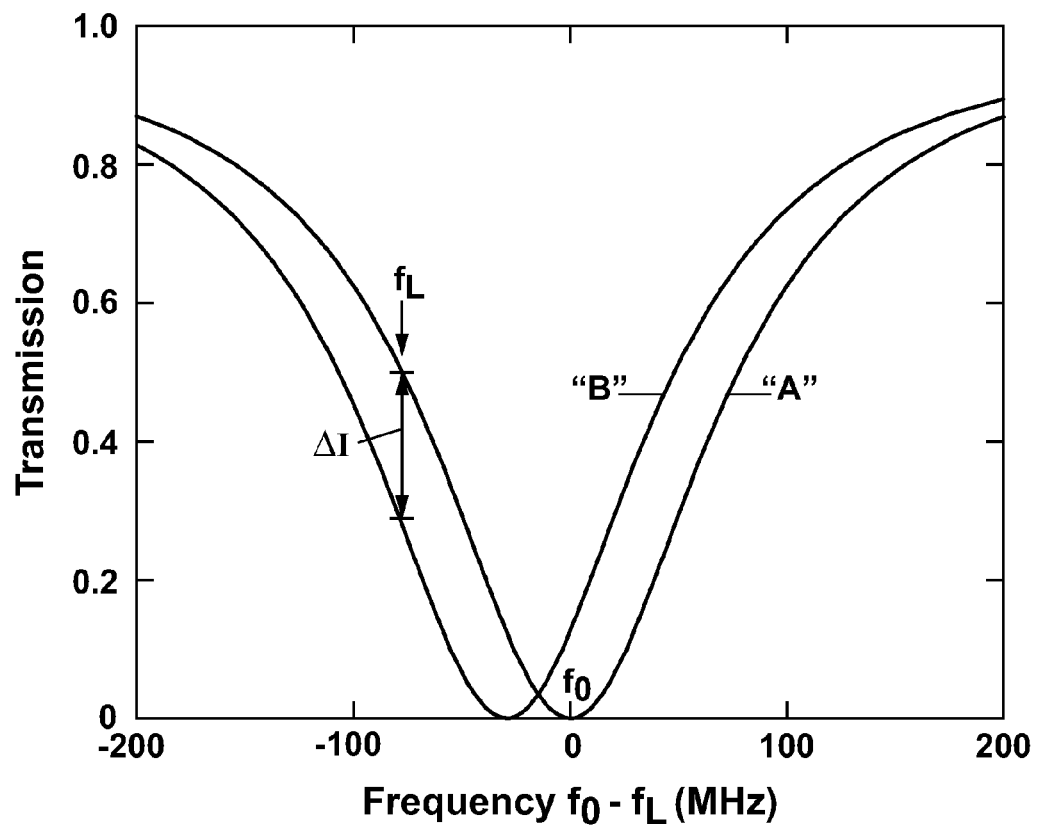
FIG. 2 shows characteristic curves of an optical resonator without heating by infrared radiation (curve "A"), and the same resonator which is shifted in frequency due to heating by infrared radiation (curve "B").

The coupling of the light 22 between the optical waveguide 20 and the optical resonator 12 will depend upon the exact frequency $f_L$ of the light 22 in the optical waveguide 20 relative to the resonant frequency $f_0$ of the optical resonator 12. This can be understood with reference to FIG. 2. In FIG. 2 as the frequency $f_L$ of the light 22 in the optical waveguide 20 is varied about the resonant frequency $f_0$, a characteristic curve is generated for the light 22 transmitted through the optical waveguide 20 and detected with the photodetector 30. This characteristic curve, which is labelled "A" in FIG. 2, has an inverse Lorentzian shape with a full-width at half maximum (FWHM) which depends upon a quality factor Q of the optical resonator 12. When the frequency $f_L$ of the light 22 in the optical waveguide 20 is tuned to coincide with the resonant frequency $f_0$, a minimum amount of the light 22 will be detected by the photodetector 30 since substantially all of the light 22 is being coupled into the optical resonator 12. Detuning the frequency $f_L$ of the light 22 away from the resonant frequency $f_0$ reduces the coupling between the optical waveguide 20 and resonator 12, thereby increasing the amount of light detected by the photodetector 30 as shown in FIG. 2.

If the frequency $f_L$ of the light 22 is fixed at a particular reference point on the characteristic curve labelled "A" in FIG. 2, then any change in the resonant frequency $f_0$ of the optical resonator 12 due to temperature can be measured simply by monitoring the amount of the light 22 exiting the optical waveguide 20 using the photodetector 30. This can be seen, for example, with the frequency $f_L$ being set at a 50% transmission point on the characteristic curve "A" as indicated by the downward-pointing arrow in FIG. 2. Any change in the resonant frequency $f_0$ of the optical resonator 12 will shift the characteristic curve "A" and this will result in a change in the amount of light 22 transmitted through the waveguide 20 and detected by the photodetector 30. The change in the resonant frequency $f_0$ can occur from direct heating of the optical resonator 12 due to incident infrared radiation 100. An interior portion of the optical resonator 12, which is not necessary for propagation of the light 22' in the resonator 12, can be left in place as shown in FIG. 1 to increase the volume of material which absorbs the incident infrared radiation 100, thereby increasing the heating of the resonator 12.

Figure 5:
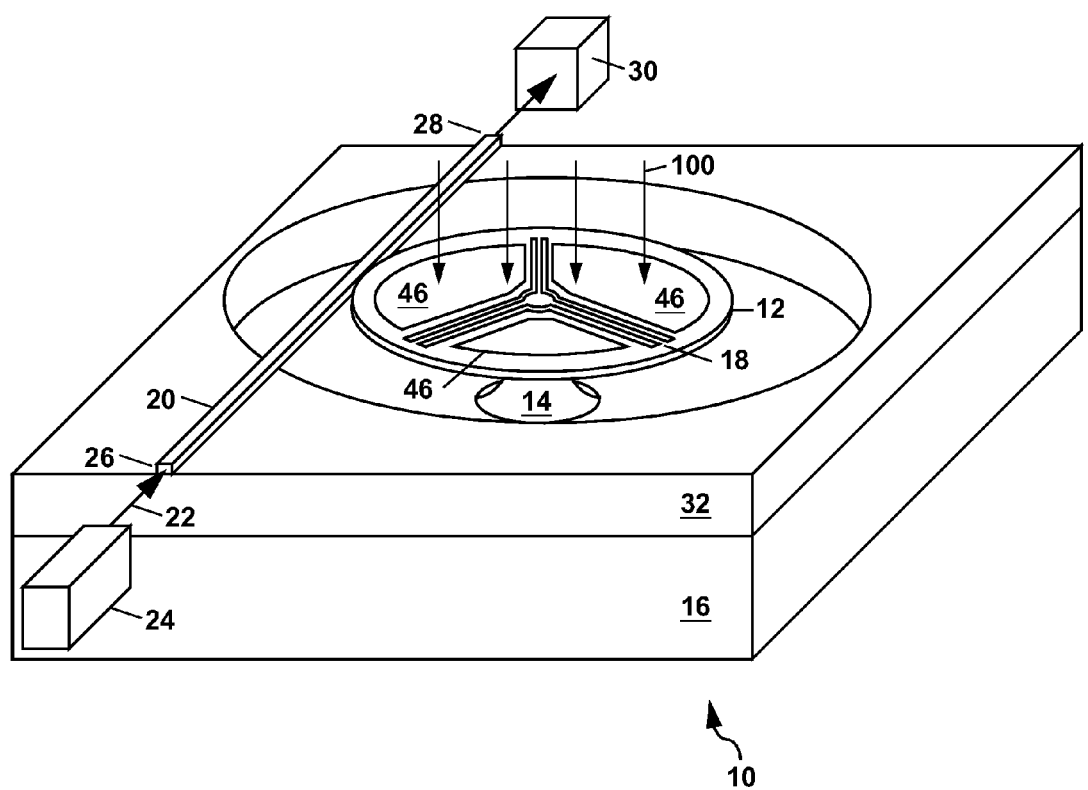
FIG. 5 shows a schematic perspective view of a second example of the thermal microphotonic sensor of the present invention.
Figure 7I:
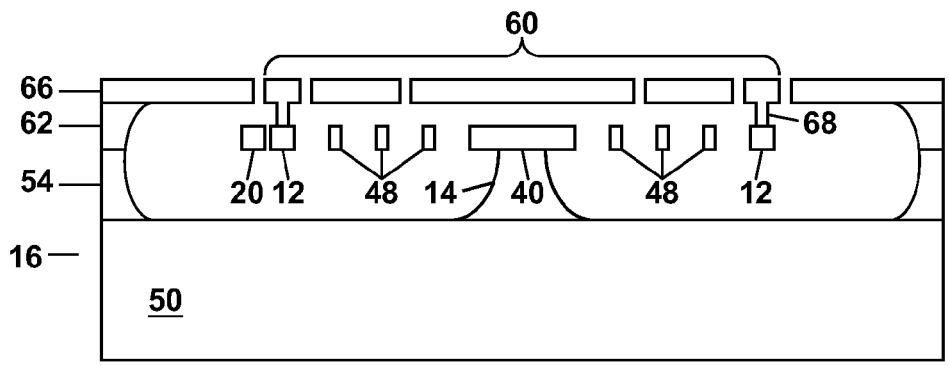
Figure 8:
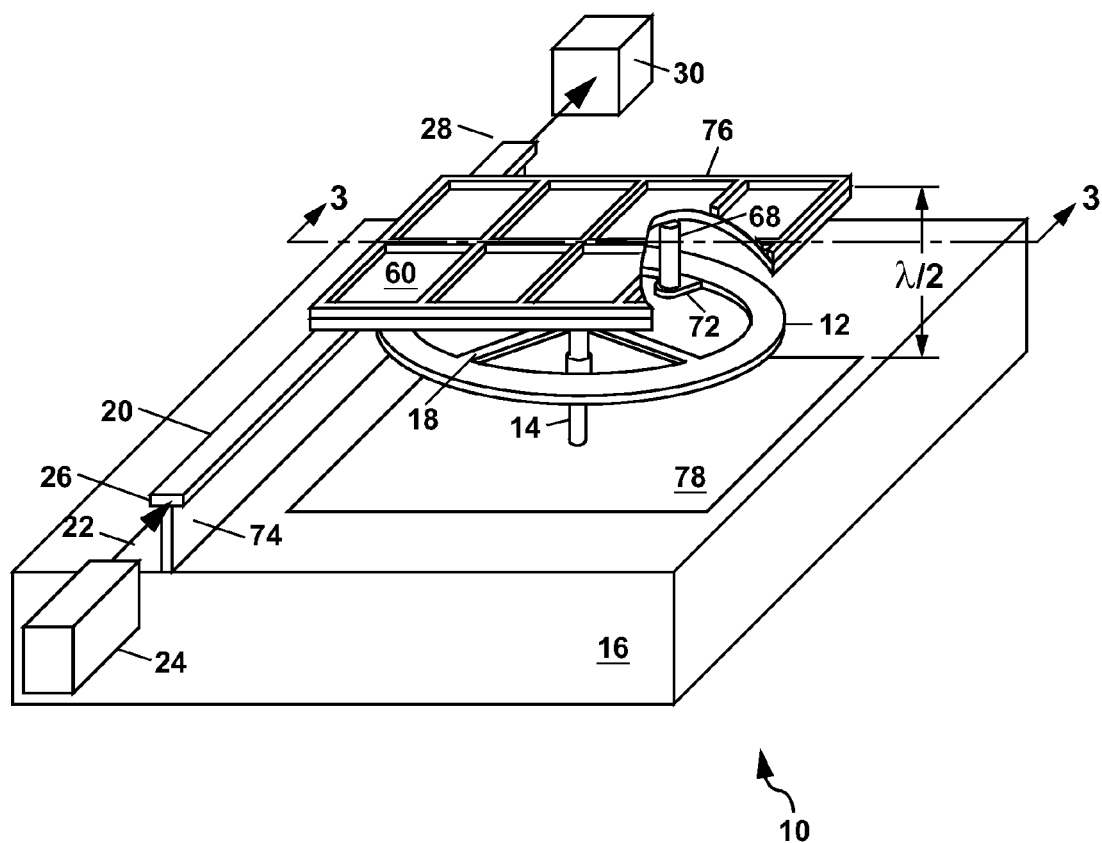
FIG. 8 shows a schematic perspective view of a fourth example of the thermal microphotonic sensor of the present invention.

In other embodiments of the present invention, an infrared absorber can be provided in the device 10 to absorb the infrared radiation 100 producing heating therein which can then be thermally coupled from the infrared absorber to the optical resonator 12 to shift the resonant frequency therein. The infrared absorber can comprise an infrared-absorbing coating 46 on a surface of the optical resonator as shown in FIG. 5, or an infrared-absorbing plate 60 supported on the optical resonator 12 as shown in FIGS. 7I, 8 and 17C. This shift in the characteristic curve for the resonator 12 with heating due to the infrared radiation 100 can be on the order of 1-10 GHz/° C., and is illustrated in FIG. 2 by the curve labelled "B." Here, a change in intensity ΔI of the light 22 which is detected by the photodetector 30 is indicated by a double-headed arrow. The term "infrared radiation" as used herein is defined as being electromagnetic radiation with a wavelength that is in a range of 0.7 μm to 1000 μm.

Although not shown in FIG. 1, a reference optical resonator can be optionally provided in the thermal microphotonic sensor. The reference optical resonator, which can be formed substantially identically to the optical resonator except for being shielded from heating by the infrared radiation is useful to frequency stabilize the laser 24 by locking it to a particular point on the characteristic curve of the reference optical resonator. This can be done by incorporating the reference optical resonator into a feedback loop which stabilizes the frequency of the laser 24. The reference optical resonator can also provide a reference for measuring the shift in the resonant frequency of the optical resonator 12 due to heating by the sensed infrared radiation.

The thermal microphotonic sensor 10 in FIG. 1 can be formed using conventional semiconductor micromachining processes which are well known in the art. This is schematically illustrated by a series of cross-section views in FIGS. 3A-3F which are taken along the section line 1-1 in FIG. 1 during various steps in the fabrication of the thermal microphotonic sensor 10. Those skilled in the art will understand that only the essential processing steps are illustrated in FIGS. 3A-3F. Many other processing steps, which are well-known to those skilled in semiconductor micromachining, have been omitted including steps for mask formation and removal, photolithography, and cleaning.

Figure 3A:
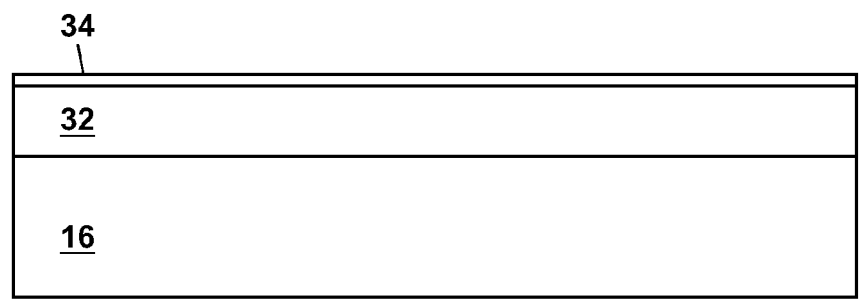
FIGS. 3A-3F show schematic cross-section views along the section line 1-1 in FIG. 1 to illustrate fabrication of the device of FIG. 1.

In FIG. 3A, a substrate 16 is provided on which are blanket deposited a layer 32 of silicon oxide and a layer of silicon nitride 34. The substrate 16 can comprise, for example, a semiconductor such as silicon (e.g. a silicon wafer, or a portion thereof). The layers 32 and 34 can be deposited by chemical vapor deposition (CVD) at a temperature in the range of 450-750° C. depending upon whether the layers 32 and 34 are deposited by plasma-enhanced CVD or low-pressure CVD. The silicon oxide layer 32 can also be formed as a thermal oxide in which a portion of a silicon substrate 16 is thermally oxidized and converted into silicon dioxide by exposure of the silicon substrate 16 to an oxygen or moisture (e.g. steam) at a high temperature of about 1050° C. In some cases, the silicon oxide layer can comprise a silicate glass such as TEOS which can be deposited by CVD from the thermal decomposition of tetraethyl orthosilicate. Thus, the term "silicon oxide" as used herein is intended to include silicon dioxide ($SiO_2$) and silicate glasses such as TEOS.

After the deposition of each layer 32 and 34, a chemical-mechanical polishing (CMP) step can be used to precisely adjust the thickness of the layer 32 or 34 and also to provide a smooth surface for the layer 32 or 34. This provides smooth top and bottom surfaces for the silicon nitride layer 34 which can reduce a scattering loss of the light 22 in the optical waveguide 20 and in the optical resonator 12 which will be formed from the silicon nitride layer 34. The thickness of the silicon oxide layer 32 can be, for example, 2-5 μm; and the thickness of the silicon nitride layer 34 can be, for example, 0.2-0.3 μm.

Figure 3B:
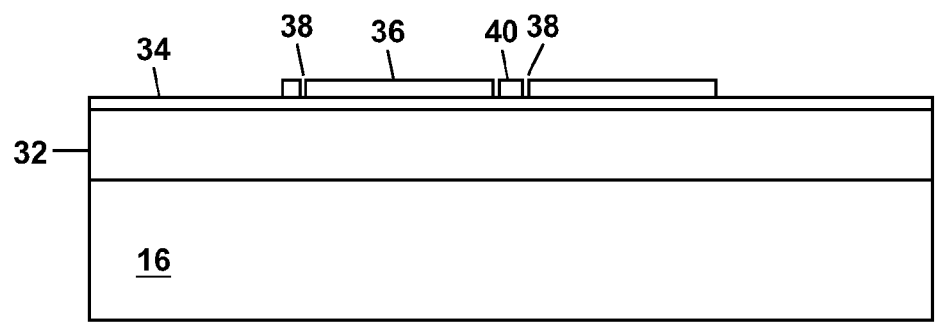

In FIG. 3B, the silicon nitride layer 34 can be patterned by providing a photolithographically-defined etch mask 36 over the silicon nitride layer 34 with a shape and openings 38 to define the optical waveguide 20, the optical resonator 12, the tethers 18 and a top 40 for the support post 14 which will be formed later. To photolithographically define the various elements formed in the silicon nitride layer 34, a deep UV photoresist can be used with a bottom anti-reflection coating (BARC). The deep UV photoresist allows submicron features to be defined in the silicon nitride layer 34, including a submicron air gap formed between the waveguide 20 and the resonator 12.

The sidewalls of the photoresist openings 38 can be smoothed, if needed, to produce smoother sidewalls for the optical waveguide 20 and the optical resonator 12 to reduce a scattering loss for the light 22. An additional smoothing step can be used to smooth the sidewalls of the waveguide 20 and the resonator 12 after these elements are formed by etching any asperites in the silicon nitride layer 34. Photoresist and silicon nitride smoothing techniques, which can be used to fabricate the thermal microphotonic sensor 10 of the present invention, are well known in the art (see e.g. M. J. Shaw, et al., "Fabrication Techniques for Low Loss Silicon Nitride Waveguides," *Proceedings of the Society of PhotoOptical Instrumentation Engineers (SPIE)*, vol. 5720, pp. 109-118, 2005). Smoothing of the photoresist can be performed, for example, heating (i.e. re-flowing) the photoresist or by etching the sidewalls of the photoresist in the openings 38 using an hydrogen bromide/oxygen (HBr—$O_2$) plasma. Smoothing of the silicon nitride waveguide 20 and resonator 12 can be performed by wet etching in a hot phosphoric acid bath at 180° C., or alternately by exposing the waveguide 20 and resonator 12 to steam at a temperature of 1050° C. to oxidize any asperites in the silicon nitride followed by etching with hydrofluoric acid (HF) to remove the oxidized asperites.

Figure 3C:
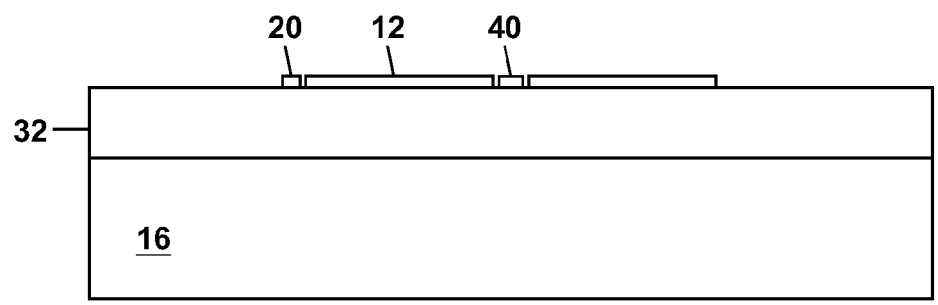

In FIG. 3C, to define the various elements 12, 18, 20 and 40 being formed from the silicon nitride layer 34, a reactive ion etching (RIE) step can be used. The RIE step etches away portions of the silicon nitride layer 34 which are exposed by the etch mask 36.

The optical waveguide 20 can be, for example, about 1 μm wide, with the optical resonator 12 being, for example, 5-100 μm in diameter. The tethers 18 can be, for example, 0.05-0.2 μm wide; and the top 40 for the support post 14 can be up to a few microns wide. A spacing between the optical waveguide 20 and the optical resonator 12 can be, for example, about 0.2 μm.

After etching the silicon nitride layer 34 to form the various elements 12, 18, 20 and 40, an annealing step can be performed at a high temperature of 1050-1200° C. for up to several hours. A separate annealing step can also be performed to anneal the silicon oxide layer 32 prior to deposition of the silicon nitride layer 34. These annealing steps can improve the light transmission in the optical waveguide 20 and also in the optical resonator 12 by reducing the presence of molecular H—O bonds in the silicon oxide layer 32 beneath the waveguide 20 and by reducing molecular H—N and Si—H bonds in the silicon nitride used to form the waveguide 20 and the resonator 12. These molecular bonds, if not reduced, will absorb some of the light 22 to reduce the transmission in the waveguide 20 and also to degrade a quality factor, Q, of the resonator 12.

Figure 3D:
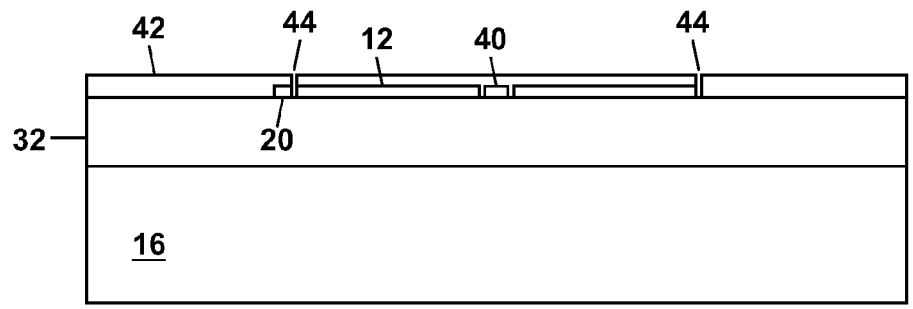

In FIG. 3D, a second etch mask 42 can be formed from the deep UV photoresist with an annular opening 44 which is centered about the periphery of the optical resonator 12.

Figure 3E:
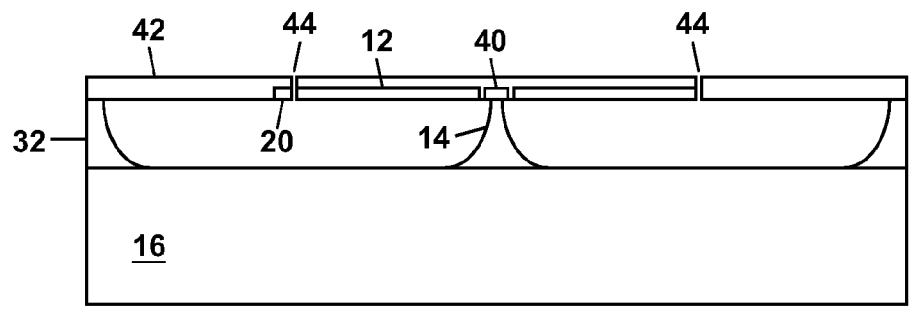

In FIG. 3E, the silicon oxide layer 32 can be etched away beneath the optical resonator 12, the tethers 18 and the optical waveguide 20 using an isotropic wet etchant comprising HF which is introduced through the annular opening 44 by immersing the substrate 16 into the HF etchant. The HF etching step can be timed to leave a portion of the silicon oxide layer 32 in place beneath the support post 40 to complete the support post 14. Some of the silicon oxide layer 32 is also left in place to support the optical waveguide 20 which is now suspended above the substrate 16 in the vicinity of the optical resonator 12 as shown in FIG. 1. The silicon substrate 16 and the various elements 12, 18, 20 and 40 formed from the silicon nitride layer 34 are not substantially chemically attacked by the HF etchant.

Figure 3F:
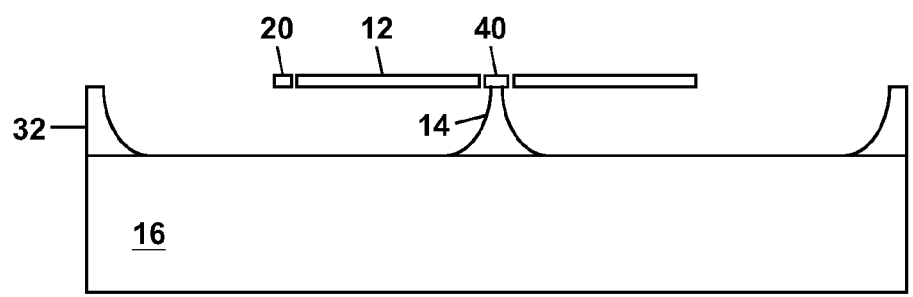

In FIG. 3F, the second etch mask 42 is removed. This leaves the optical resonator 12 suspended above the substrate 16 by the support post 14 and tethers 18 as shown in FIG. 1.

Figure 4:
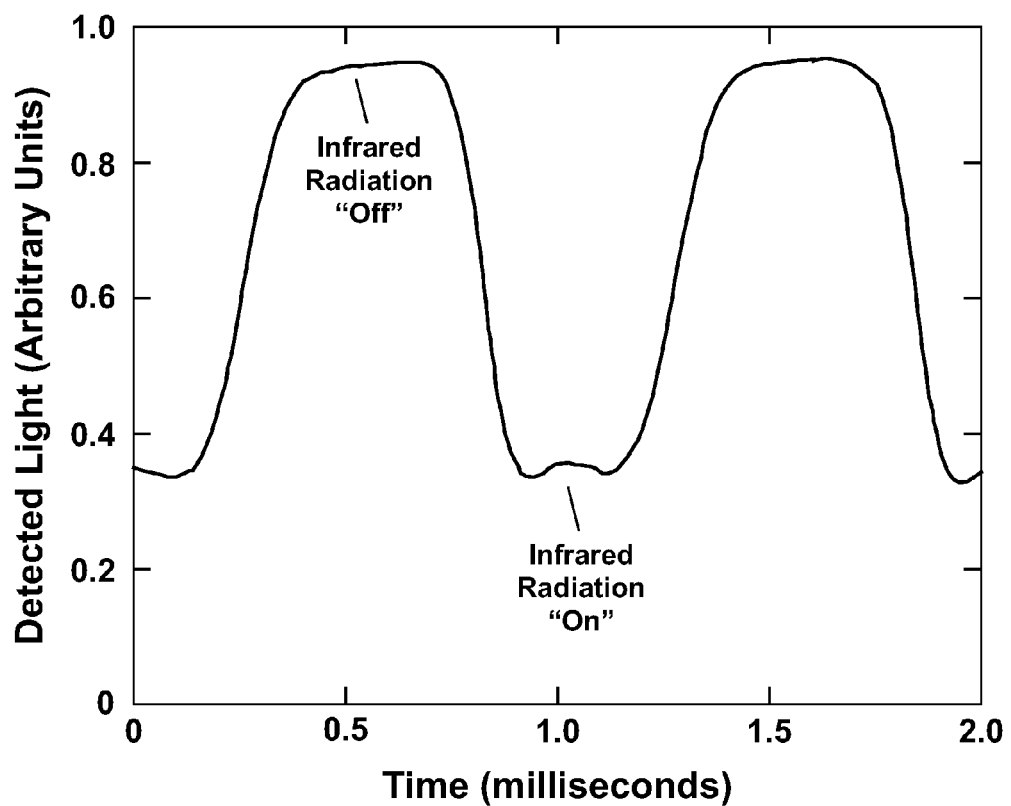
FIG. 4 shows a response curve for the thermal microphotonic sensor of FIG. 1 with infrared radiation at a wavelength of 10 μm being repeatedly switched "on" and "off."

FIG. 4 shows a response curve for the thermal microphotonic sensor 10 of FIG. 1 using about 1 microWatt (μW) of 10.6-μm infrared radiation 100 from a carbon dioxide laser 24 incident onto a top surface of a 25-μm-diameter optical resonator 12. The 10.6-μm infrared radiation 100 is absorbed into the silicon nitride material forming the resonator 12. The silicon nitride is highly absorptive to infrared radiation at wavelengths in the 8-12 μm range and is, at the same time, transparent to guide the light 22 from the laser 24 at a wavelength of 1.508 μm in both the optical waveguide 20 and the resonator 12.

In FIG. 4, the incident 10.6-μm infrared radiation 100 is repeatedly switched "on" and "off" at a 1 millisecond repetition rate using a light chopper. This shifts the resonant frequency $f_0$ of the optical resonator 12 back and forth as the resonator 12 repeatedly heats up and cools down in response to the incident 10.6-μm infrared radiation 100. The light 22 at the photodetector 30 is at a maximum when the infrared radiation 100 is switched "off" and is at a minimum when the infrared radiation 100 is switched "on." This response curve in FIG. 4 shows the utility of the device 10 for detecting the infrared radiation 100 in the 8-12 μm range.

The absorption of the 10.6-μm infrared radiation 100 by the 0.2-μm-thick silicon nitride resonator 12 used to obtain the response curve of FIG. 4 is estimated to be on the order of 10%, with the resonator Q being about $10^4$, and with the thermal isolation of the resonator 12 from the substrate 16 being limited by conduction through the air so that the thermal conductance G is about $10^{-6}$ W-K$^{-1}$. The sensitivity of the device 10 of FIG. 1 can be further improved by operating the device 10 under vacuum, by increasing the Q of the resonator 12, and by increasing the absorption of the infrared radiation 100.

The absorption of the infrared radiation 100 can be increased using an infrared absorber which is tailored to highly absorb infrared radiation 100 over a particular wavelength range. The infrared absorber can comprise an infrared-absorbing coating 46 covering at least a part of the optical resonator 12. This is schematically illustrated in the perspective view of FIG. 5 which shows a second example of a thermal microphotonic sensor 10 formed according to the present invention.

The infrared-absorbing coating 46 in the device 10 of FIG. 5 can comprise a material such as a metal (e.g. tungsten) which can be deposited over the optical resonator 12 during fabrication of the device 10. Virtually any material can be used for the infrared-absorbing coating 46 which has a relatively high absorption of the infrared radiation 100 over a particular wavelength range of interest and which can be deposited in a relatively thin layer on the order of about 1 μm or less. The infrared-absorbing coating 46 can be deposited by any method known to the art including evaporation, sputtering, CVD, spinning onto the substrate 16, ink-jet deposition, etc. The infrared-absorbing coating 46 can be patterned during deposition (e.g. using a shadow mask), or can be patterned after deposition (e.g. by lift-off or by an RIE step). The infrared-absorbing coating 46 can have a size and shape to enhance the absorption of the infrared radiation 100 at a particular wavelength, or wavelength range. The infrared-absorbing coating 46 is preferably omitted from an outer edge of the resonator 12 as shown in FIG. 5 to prevent any attenuation or scattering of the portion 22' of the light 22 circulating in the resonator 12 due to the presence of the coating 46.

Figure 6:
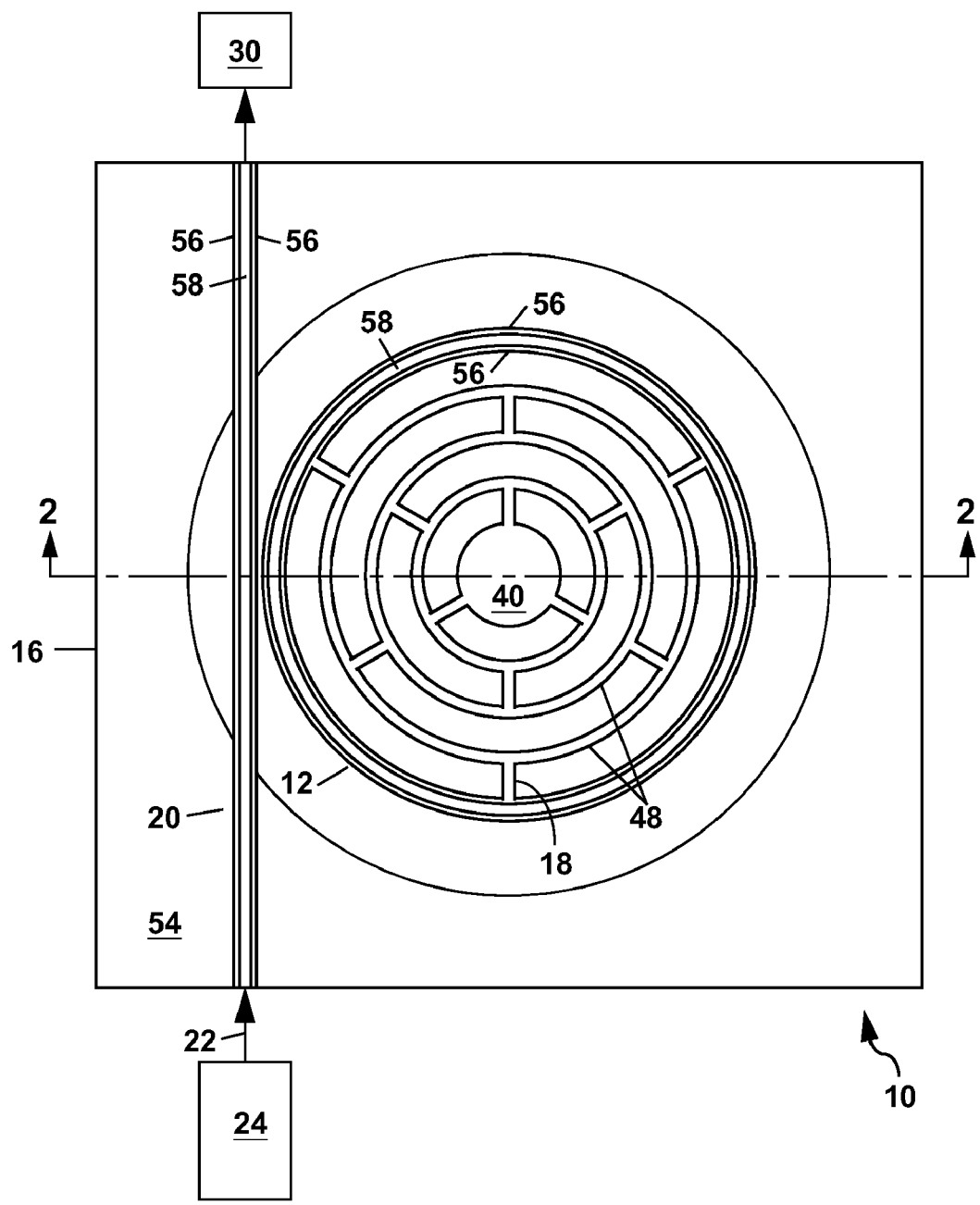
FIG. 6 shows a schematic plan view of a third example of the thermal microphotonic sensor of the present invention.

Although the tethers 18 in the first and second examples of the present invention extend radially outward from the support post 14, in other embodiments of the present invention, a more circuitous thermal path can be used to further increase the thermal isolation of the optical resonator 12 from the substrate 12. FIG. 6 shows a schematic plan view of a third example of the thermal microphotonic sensor 10 of the present invention in which a plurality of tethers 18 are interconnected with one or more concentric rings 48 to provide the more circuitous thermal path between the optical resonator 12 on the support post 14.

In the example of FIG. 6, the optical waveguide 20 and the optical resonator 12 both comprise monocrystalline silicon; and the tethers 18 and the concentric rings 48 comprise silicon dioxide. The use of silicon dioxide for the tethers 18 and concentric rings 48 together with the more circuitous thermal path provided by these elements 18 and 48 can greatly increase the thermal isolation of the optical resonator 12 from the substrate 16. Calculations with an ANSYS finite element thermal model indicate that a thermal conductance $G=1.2\times 10^{-8}$ W-K$^{-1}$ can be attained for a 10-μm-diameter resonator 12 using a series of interconnected silicon dioxide tethers 18 and silicon dioxide concentric rings 48 which are each 0.05 μm wide and 0.25 μm thick.

Fabrication of the device 10 of FIG. 6 will now be described with reference to FIGS. 7A-7I which show a schematic cross-section views along the section line 2-2 in FIG. 6.

Figure 7A:
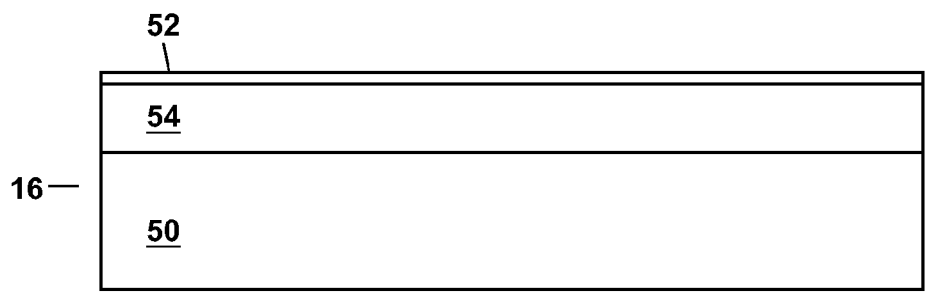
FIGS. 7A-7F show schematic cross-section views along the section line 2-2 in FIG. 6 to illustrate fabrication of the device of FIG. 6.

In FIG. 7A, a substrate 16 can be provided which comprises a commercially-available silicon-on-insulator substrate having a monocrystalline silicon body 50 and a monocrystalline silicon layer 52 sandwiched about a silicon dioxide layer 54. The monocrystalline silicon layer 52 can be, for example, 0.2-0.3 μm thick; and the silicon dioxide layer 54 can be, for example, 1-5 μm thick.

Figure 7B:
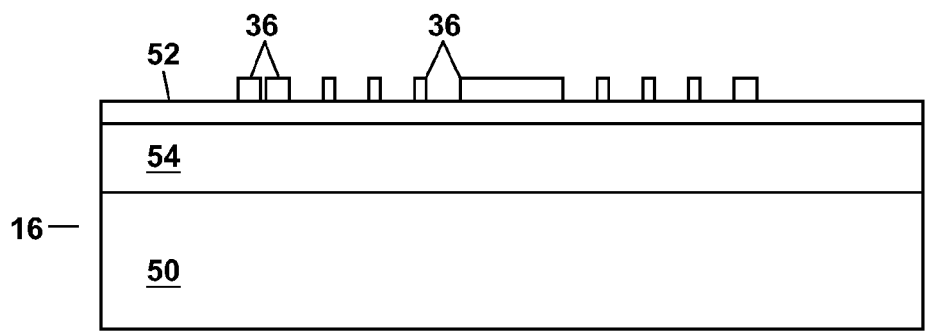
Figure 7C:
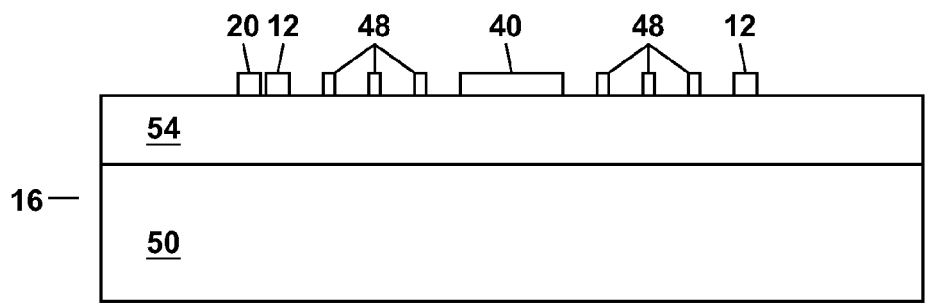

In FIG. 7B, a photolithographically-defined etch mask 36 can be formed on the monocrystalline silicon layer 52. The etch mask 36 can be as previously described with reference to FIG. 3B. A reactive ion etching (RIE) step can then be used to pattern the monocrystalline silicon layer 52 to define the waveguide 20, resonator 12, tethers 18, concentric rings 48 and the top 40 for the support post 14. The etch mask 36 can then be removed to leave the various elements 12, 18, 20, 40 and 48 formed from the monocrystalline silicon layer 40 as shown in FIG. 7C.

Figure 7D:
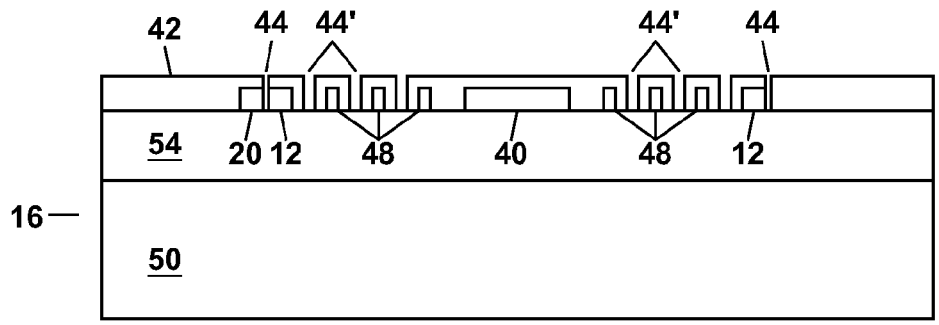

In FIG. 7D, a second etch mask 42 can be provided over the substrate 16 as previously described with reference to FIG. 3D. The second etch mask 42 includes an annular opening 44 which is centered about the periphery of the optical resonator 12. A plurality of additional openings 44' can also be provided between the resonator 12 and the top 40 of the support post 14 to provide a faster etching time for removing the silicon dioxide layer 54.

Figure 7E:
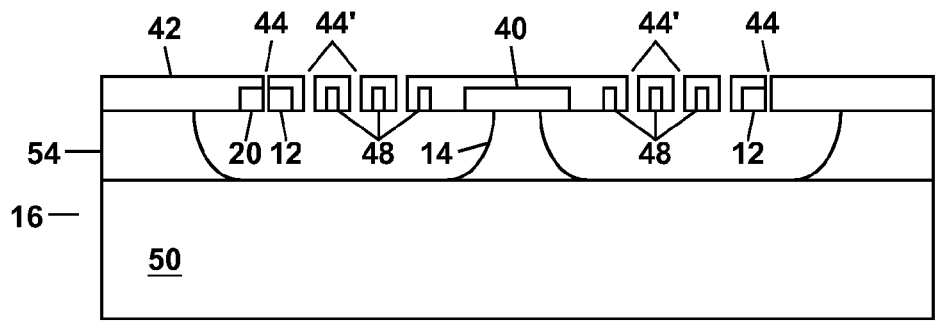

In FIG. 7E, the silicon dioxide layer 54 can be etched away beneath the various elements 12, 18, 20 and 48 as previously described with reference to FIG. 3E using the isotropic HF etchant. The etching can be timed and stopped when the silicon dioxide layer 54 is laterally etched back to the top 40 of the support post 14 or beyond as shown in FIG. 7E. This completes the formation of the support post 14. A part of the silicon dioxide layer 54 is also left in place to suspend the optical waveguide 20 as shown in FIG. 6.

Figure 7F:
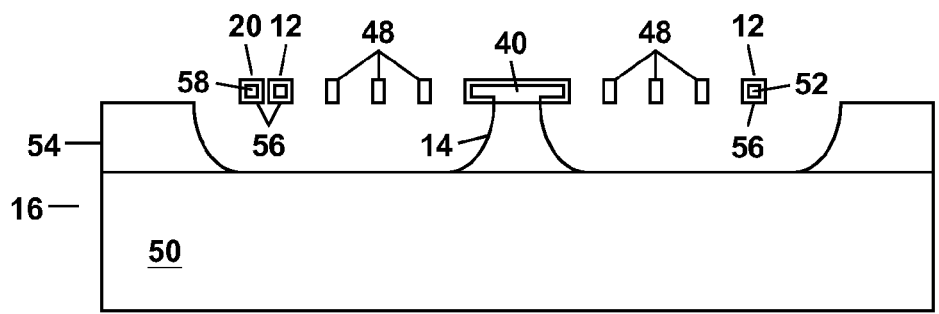

In FIG. 7F, the second etch mask 42 is removed. The substrate 16 containing the optical resonator 12 suspended above the substrate 16 by the support post 14, tethers 18 and concentric rings 48 can then be annealed in an oxygen ambient at a high temperature of 900-1000° C. for sufficient time to completely oxidize the monocrystalline silicon in the 50-nanometers-wide tethers 18 and concentric rings 48, thereby converting these elements to silicon dioxide. This high-temperature oxidation step also converts an exposed outer portion of the optical waveguide 20 and the optical resonator 12 to silicon dioxide, with the silicon dioxide being about 25 nanometers thick. This forms a silicon dioxide cladding 56 over a monocrystalline silicon core 58 for the both the waveguide 20 and the resonator 12 which reduces a transmission loss of the light 22 in both of these elements.

Figure 7G:
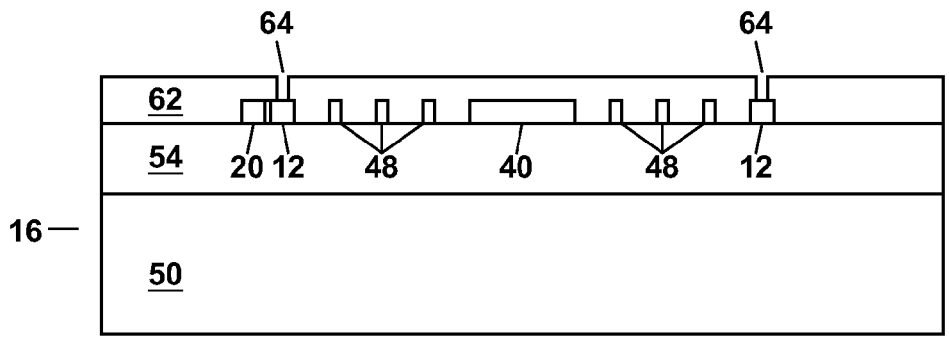
FIGS. 7G-7I show schematic cross-section views along the section line 2-2 in FIG. 6 to illustrate additional process steps which can be used to add an infrared-absorbing plate to the device of FIG. 6.

In the example of FIG. 6, the optical resonator 12 can be directly heated by the incident infrared radiation 100 which is absorbed by the monocrystalline silicon and silicon dioxide materials forming the resonator 12. Alternately, an infrared absorber can be provided in the apparatus 10 to absorb the incident infrared radiation 100 and to transfer the resultant heat generated in the infrared absorber to the optical resonator 12. This can be done using an infrared-absorbing plate 60 which can be supported on the optical resonator 12. The addition of the infrared-absorbing plate 60 can be provided, for example, after the step of FIG. 7C. This can be done by initially blanket depositing a layer 62 of silicon dioxide or a silicate glass such as TEOS over the patterned elements 12, 20, 40 and 48 formed from the monocrystalline silicon layer 52 as shown in FIG. 7G. The layer 62 can be, for example, 1-2 μm thick. After blanket deposition of the layer 62 by CVD, the layer 62 can be planarized by a CMP step. A plurality of openings 64 can then be etched down through the layer 62 to expose a portion of the optical resonator 12.

Figure 7H:
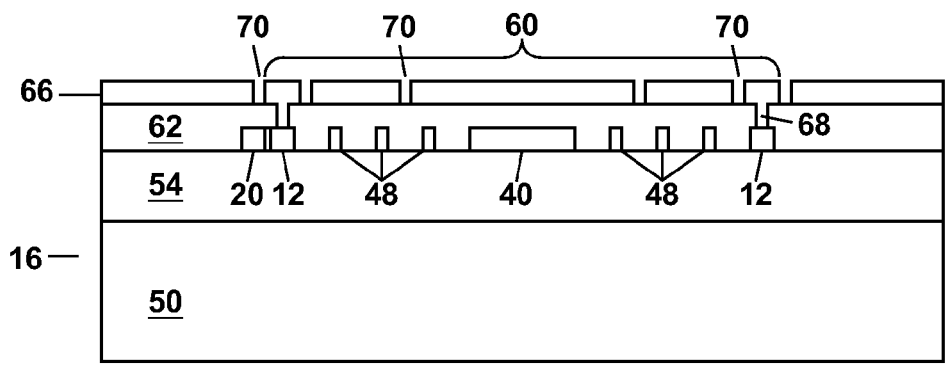

In FIG. 7H, a layer 66 of silicon nitride can be deposited by CVD to fill in the openings 64, thereby forming legs 68 which will support the infrared-absorbing plate 60 on the resonator 12. The silicon nitride layer 66, which can have a thickness of, for example, 0.2-1 μm, can then be patterned by an RIE etch step to form the infrared-absorbing plate 60. The shape of the infrared-absorbing plate 60 can be circular, polygonal, elliptical, oval, or any arbitrary shape. In some cases, the shape of the infrared-absorbing plate 60 can be selected to provide an enhanced absorption of the infrared radiation 100 at a particular wavelength or wavelength range. As an example, the infrared-absorbing plate or a metal coating thereon can be shaped to form a bow-tie antenna or a patch antenna to receive the infrared radiation 100 at a particular wavelength determined by the size of the antenna. A ground plane (not shown) can be formed below the antenna by using a doped substrate 16, or alternately by providing a metal layer (e.g. tungsten) on the substrate 16 beneath the antenna (see FIG. 8).

After depositing the silicon nitride layer 66, a plurality of openings 70 can be etched through the silicon nitride layer 66 and around the infrared-absorbing plate 60 during formation of the plate 60 as shown in FIG. 7H. This can be done with an RIE step. The openings 70 will allow the infrared-absorbing plate 60 and a remainder of the silicon nitride layer 66 to be used as an etch mask for removing the underlying layers 54 and 62 using the HF etchant. The number and shape of the openings 70 can be selected to allow the HF etchant to completely remove the layers 54 and 62 surrounding the resonator 12, the tethers 18, the waveguide 20 and the concentric rings 48 while leaving a portion of the layers 54 and 62 in place to form the support post 14 and to support the optical waveguide 20 and the remainder of the silicon nitride layer 66. This is shown in FIG. 7I. The remainder of the silicon nitride layer 66 can be left in place in the completed device 10.

A high-temperature oxidation step in an oxygen ambient can then be performed as previously described with reference to FIG. 7F to oxidize the monocrystalline silicon in the tethers 18 and concentric rings 48 and thereby convert these elements into silicon dioxide. This greatly reduces the thermal conductivity of these elements 18 and 48 since the thermal conductivity of silicon dioxide is two orders of magnitude lower than that for monocrystalline silicon. As previously discussed, this high-temperature oxidation step also forms a thin (e.g. 25 nm) silicon dioxide cladding 56 over both the waveguide 20 and the resonator 12 by converting a portion of the monocrystalline silicon material in these elements 20 and 12 into silicon dioxide.

In other embodiments of the present invention, the optical resonator 12 can be provided with a plurality of tabs 72 (see FIG. 8) extending radially inward from the resonator 12, with the infrared-absorbing plate 60 being supported on the tabs 72. These tabs 72 can be formed from the monocrystalline silicon layer 52; or alternately they can be formed from deposited silicon nitride (e.g. during formation of the legs 68).

FIG. 8 shows a schematic perspective view of a fourth example of the thermal microphotonic sensor 10 of the present invention. In the example of FIG. 8, the optical waveguide 20 comprises silicon nitride and is supported above the substrate 16 on a silicon oxide base 74. A silicon oxide support post 14 is also used to suspend the optical resonator 12 above the substrate 16, which can comprise silicon. In this example of the present invention, a silicon nitride infrared-absorbing plate 60 is supported on the resonator 12 by a plurality of legs 68 which are attached to silicon nitride tabs 72 extending inward from the optical resonator 12.

In the example of FIG. 8, a partially-transmitting mirror 76, which can comprise a metal screen as shown in FIG. 8 or alternately a thin metal layer, is provided over the infrared-absorbing plate 60; and another mirror 78 is located on the substrate 16 beneath the optical resonator 12. The mirror 76 can comprise, for example, aluminum; and the mirror 78 can comprise, for example, tungsten. Both of these metals are resistant to chemical attack by the HF etchant. The thickness of each mirror 76 and 78 can be, for example, 0.1-0.2 μm. The size of the openings in the metal screen used to form the partially-transmitting mirror 76 can be selected to provide a predetermined value for the transmission of this mirror 76 at a particular wavelength of interest for the infrared radiation 100. As an example, the openings in the metal screen can be about 3 μm square to detect infrared radiation 100 over a wavelength range of 8-12 μm for which the silicon nitride plate 60 and the silicon nitride optical resonator 12 are both strongly absorbing. The infrared-absorbing plate 60 can be, for example, about 20 μm square and 0.2 μm thick.

The mirrors 76 and 78 form a vertical resonant cavity about the infrared-absorbing plate 60 that is useful to reflect the infrared radiation 100 back and forth one or more times between the two mirrors 76 and 78. This can significantly increase the amount of the infrared radiation 100 which is absorbed into the plate 60 and thermally coupled into the optical resonator 12. It also significantly increases the amount of the infrared radiation 100 which is directly absorbed into the optical resonator 12. A spacing of the mirrors 76 and 78 can be made resonant at a particular wavelength of the infrared radiation 100 to enhance the absorption of this wavelength of the infrared radiation 100 in the sensor 10. This can be done by separating the mirrors 76 and 78 by a distance which is substantially equal to one-half of the wavelength (i.e. $\lambda/2$) of the infrared radiation 100. Thus, to detect infrared radiation 100 in the 8-12 μm wavelength range, the separation of the mirrors 76 and 78 can be about 4-5 μm.

In the example of the thermal microphotonic sensor 10 in FIG. 8, the optical resonator can be annular with an outer radius of 8 μm, a width of 2.5 μm, and a thickness of 0.25 μm. The tethers can each be 0.2 μm wide and 0.25 μm thick. The silicon oxide support post 14 can be, for example, 0.5 μm diameter and 2 μm high. The legs 68 supporting the infrared-absorbing plate 60 and thermally coupling the plate 60 to the resonator 12 can be, for example, 0.5-1 μm in diameter and 2

µm high. The optical waveguide 20 can be about 1 µm wide and 0.2-0.25 µm thick, with the silicon oxide base 74 being 2 µm high and 0.5 µm wide.

The fourth example of the thermal microphotonic sensor 10 can be fabricated on a silicon substrate 16 using conventional surface micromachining as will now be described with reference to FIGS. 9A-9I which show a series of schematic cross-section views along the section line 3-3 in FIG. 8.

The silicon substrate 16 can be initially prepared by forming a thermal oxide about 0.6 µm thick over each surface of the substrate, followed by deposition of a silicon nitride layer which can be, for example, 0.8 µm thick. The thermal oxide can be formed from the silicon substrate 16 by heating the substrate 16 to about 1050° C. in an oxygen or steam ambient. The silicon nitride layer can be deposited by CVD. These layers are considered herein to be a part of the substrate 16 and are not shown in FIGS. 9A-9I.

Figure 9A:
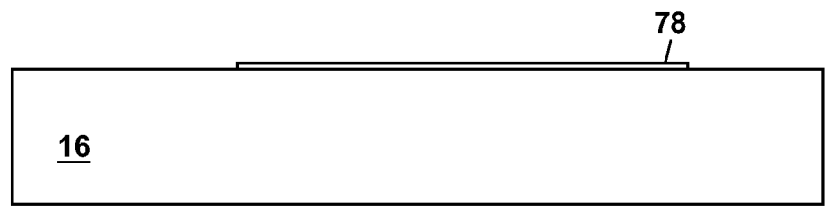
FIGS. 9A-9I show schematic cross-section views along the section line 3-3 in FIG. 8 to illustrate fabrication of the device of FIG. 8.

In FIG. 9A, a layer of tungsten can be deposited on the substrate 16 to form the mirror 78. The deposition of the tungsten can be performed by CVD or alternately by evaporation or sputtering. The mirror 78 can have a thickness of 0.1-0.2 µm.

Figure 9B:
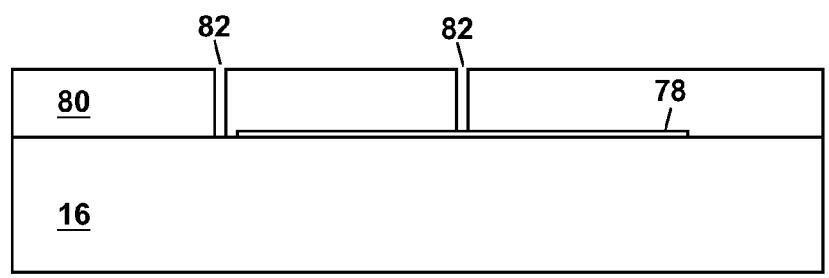

In FIG. 9B, a layer 80 of polycrystalline silicon (also termed polysilicon) can be blanket deposited over the substrate by CVD at a temperature of about 580° C. The polysilicon layer 80, which will be used as a sacrificial material and later removed with a selective etchant, can be, for example, 2 µm thick. The polysilicon layer 80 can be planarized after deposition using a CMP step. Openings 82 can then be etched through the polysilicon layer 80 at the locations where the support post 14 and the base 74 will be formed.

Figure 9C:
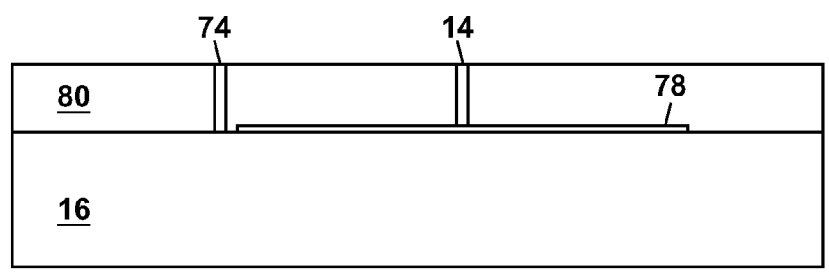

In FIG. 9C, a silicon oxide material such as TEOS or silicon dioxide can be blanket deposited by CVD to fill in the openings 82 and to blanket the polysilicon layer 80. A CMP step can be performed to remove any of the silicon oxide material which overlies the polysilicon layer 80 so that only the silicon oxide material filling in the openings 82 is left in place. This silicon oxide material will form the support post 14 and the silicon oxide base 74 as shown in FIG. 9C.

Figure 9D:
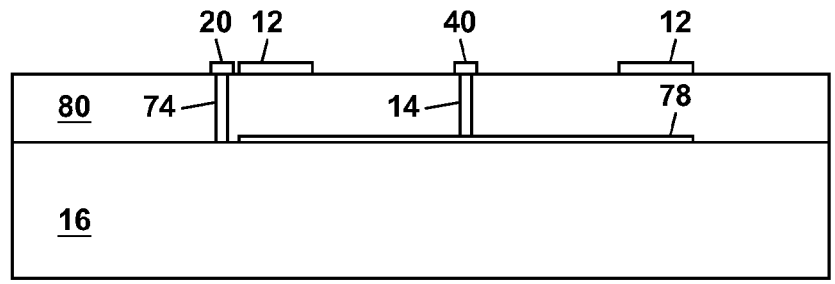

In FIG. 9D, a layer of silicon nitride can be deposited over the substrate 16 by CVD. The silicon nitride layer, which can be 0.2-0.25 µm thick, is patterned by an RIE step to form the optical resonator 12, the tethers 18, the optical waveguide 20, the top 40 of the support post 14 and the tabs 72 on the resonator 12.

Figure 9E:
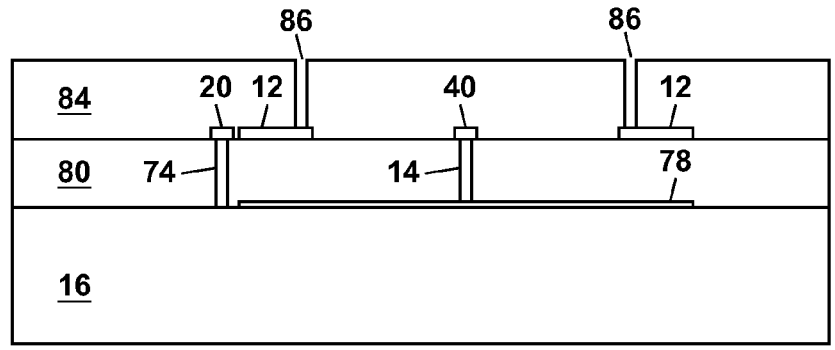

Another layer 84 of polysilicon can then be blanket deposited over the substrate 16 by CVD and planarized by a CMP step. This polysilicon layer 84 can be, for example, 2 µm thick. An RIE step can then be used to etch openings 86 down to expose the silicon nitride tabs 72 on the resonator 12 as shown in FIG. 9E.

Figure 9F:
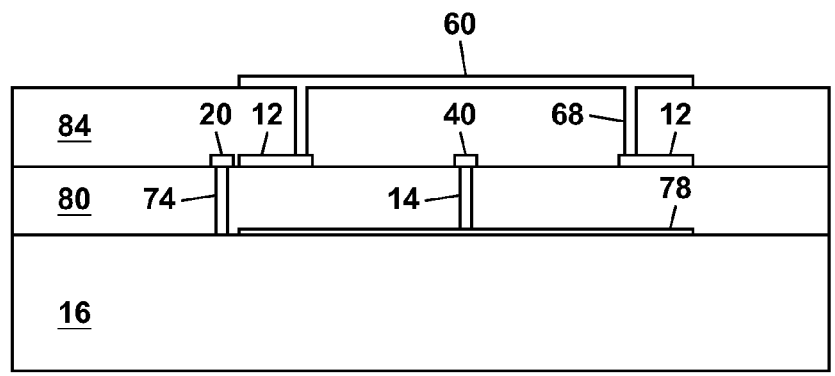

Another layer of silicon nitride about 0.2 µm can then be blanket deposited over the substrate 16 as shown in FIG. 9F. This silicon nitride layer can then be patterned by an RIE step to form the infrared-absorbing plate 60. A portion of this silicon nitride layer which fills in the openings 86 will also form the legs 68 which support the plate 60 on the optical resonator 12.

Figure 9G:
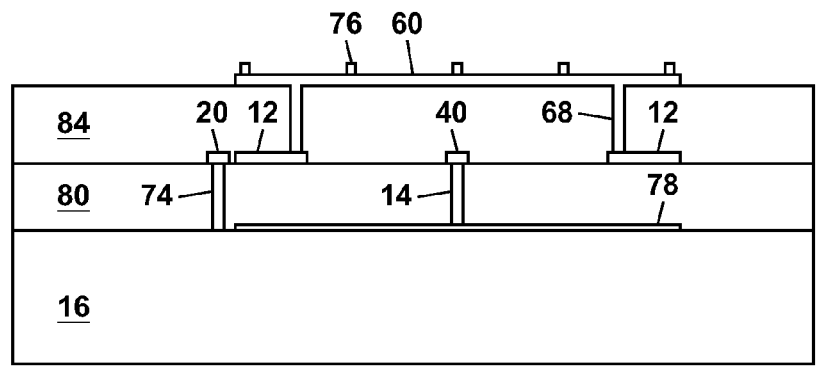

In FIG. 9G, the partially-reflecting mirror 76 can be formed over the infrared-absorbing plate 60. This can be done by depositing a 0.1-µm-thick layer of aluminum using evaporation or sputtering, and then patterning the aluminum layer using an RIE step to form the screen. Alternately, the aluminum layer can be patterned by lift-off.

Figure 9H:
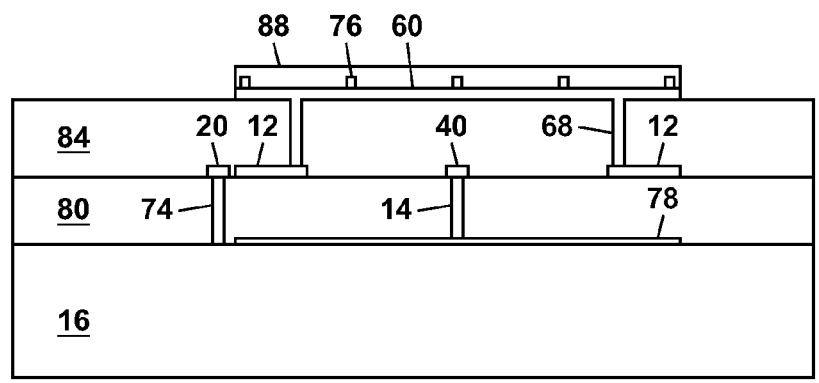
Figure 9I:
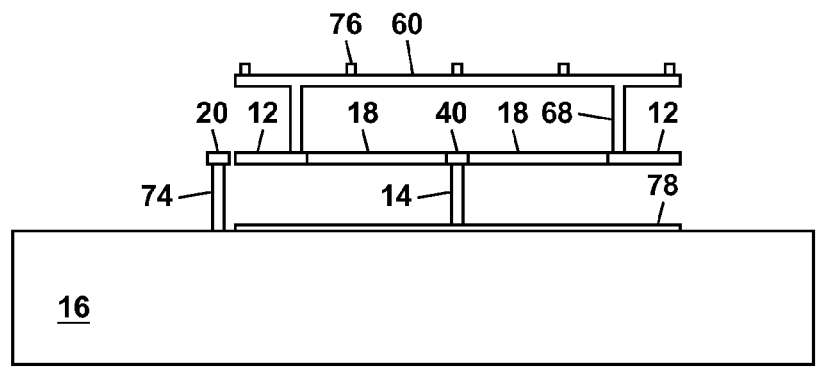

In FIG. 9H, the aluminum mirror 76 can be protected with a layer 88 of photoresist in preparation for removing the polysilicon sacrificial layers 80 and 84 using a selective wet etchant comprising potassium hydroxide (KOH). The KOH etchant will not attack the tungsten mirror 78 or the various elements formed from silicon nitride, and will only very slowly attack the silicon oxide elements 14 and 74. The thermal oxide and silicon nitride layers which blanket the silicon substrate 16 protect the silicon substrate 16 from being attacked by the KOH etchant. After removal of the polysilicon sacrificial material, the photoresist layer 88 can be removed to complete processing of the thermal microphotonic sensor 10 as shown in FIG. 9I. Alternate selective etchants which can be used to remove the polysilicon sacrificial layers 80 and 84 are, for example, ethylene diamine-pyrocatechol (EDP), tetramethyl ammonium hydroxide (TMAH), and xenon difluoride ($XeF_2$). Any selective etchant can be used which preferentially etches silicon and polysilicon while not substantially chemically attacking the other materials used to form the thermal microphotonic sensor 10.

Figure 15:
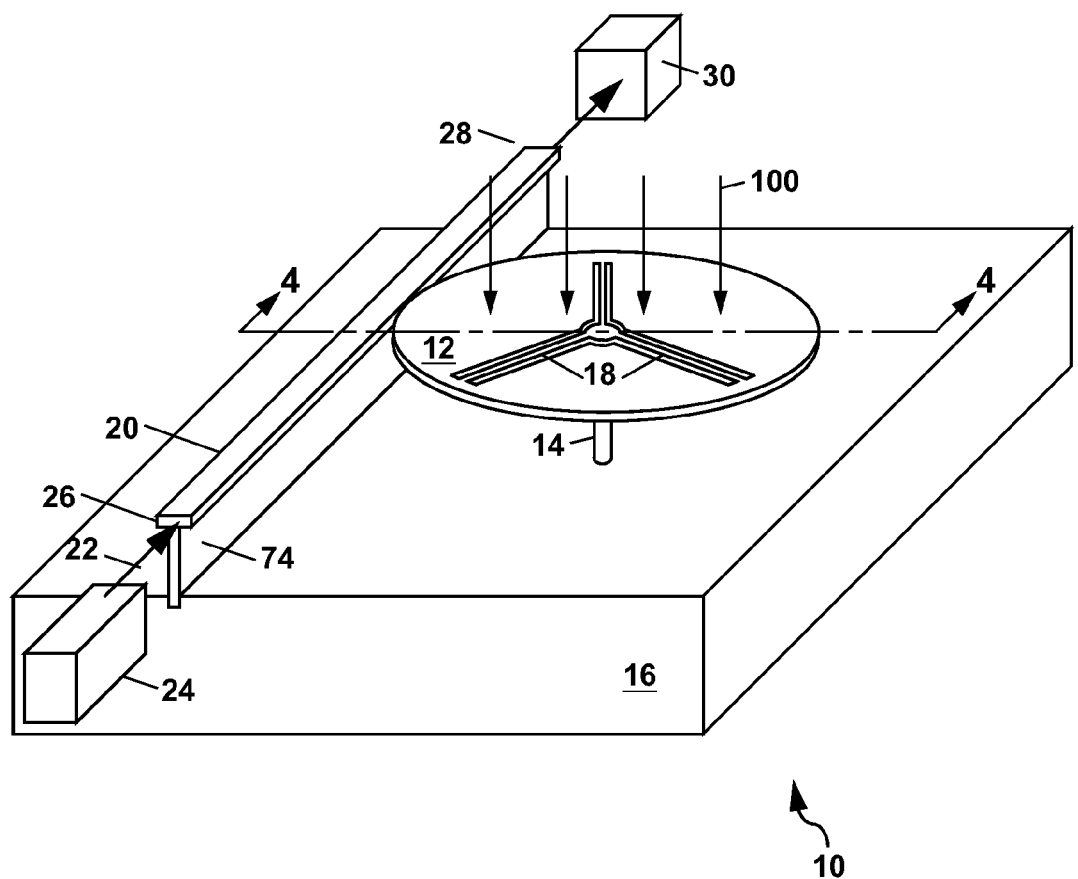
FIG. 15 shows a schematic perspective view of a fifth example of the thermal microphotonic sensor of the present invention.

FIG. 15 shows a schematic perspective view of a fifth example of the thermal microphotonic sensor 10 of the present invention which is similar to the example of FIG. 1 in using silicon nitride to form the optical resonator 12 and one or more optical waveguides 20 which are optically coupled to the resonator 12. The example of FIG. 15 differs from that of FIG. 1, however, in supporting each optical waveguide 20 on a silicon oxide base 74 over the entire length of the optical waveguide 20, and in providing a silicon oxide support post 14 for the resonator 12 which has a substantially uniform width which can be precisely-defined by anisotropic reactive ion etching.

The silicon nitride resonator 12 in the example of FIG. 15 is responsive to sense incident infrared radiation 100 in the 8-12 µm wavelength range, with the infrared radiation 100 being absorbed directly into the silicon nitride optical resonator 12 to heat the optical resonator 12 and thereby change the resonant frequency $f_0$ therein as previously described with reference to FIGS. 2 and 4. Both the optical waveguide 20 and the optical resonator 12 guide light 22 from the laser 24 at a wavelength of about 1.5 µm, with the light 22 being coupled between the waveguide 20 and resonator 12 to detect the change in the resonant frequency $f_0$ of the optical resonator 12 due to heating therein from absorption of the incident infrared radiation 100.

In the fifth example of the thermal microphotonic sensor 10 in FIG. 15, the optical resonator 12 can have an outer radius of, for example, 10 µm, and a thickness of 0.2-0.3 µm. The tethers 18 can each be, for example, 0.2 µm wide with the same thickness as the resonator 12. The silicon oxide support post 14 can be, for example, 0.5 µm diameter and 1-4 µm high. The optical waveguide 20 can be, for example, about 1 µm wide with the same thickness as the optical resonator 12. The silicon oxide base 74 for the optical waveguide 20 can be, for example, 0.5 µm wide and 1-4 µm high.

The thermal microphotonic sensor 10 of FIG. 15 can be fabricated on a silicon substrate 16 by micromachining as will now be described with reference to FIGS. 16A-16E which show a series of schematic cross-section views along the section line 4-4 in FIG. 15.

Figure 16A:
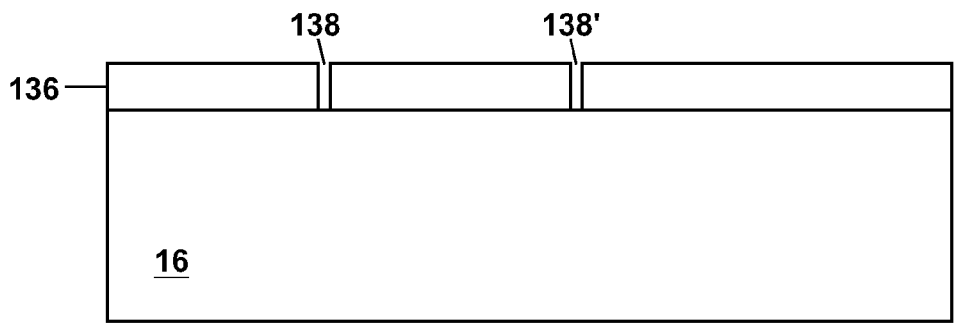
FIGS. 16A-16E show schematic cross-section views along the section line 4-4 in FIG. 15 to illustrate fabrication of the device of FIG. 15.

In FIG. 16A, a silicon substrate 16 can be initially prepared by forming a thermal oxide layer about 0.6 µm thick over each surface of the substrate 16, followed by deposition of a silicon nitride layer about 0.2 µm thick. The thermal oxide can be formed from the silicon substrate 16 by heating the substrate 16 to about 1050° C. in an oxygen or steam ambient. The silicon nitride layer can be deposited by CVD. These layers are considered herein to be a part of the substrate 16 and are not shown in FIGS. 16A-16E.

In FIG. 16A, a hard etch mask 136 can be formed over the silicon substrate 16. The hard etch mask 136 can comprise, for example, TEOS about 2 μm, with the TEOS being densified after deposition by CVD by annealing at a temperature of about 850° C. The hard etch mask 136 can be patterned using a photolithographically-defined photoresist layer (not shown) and an RIE step to define an elongate opening 138 at the location wherein a trench 140 will later be formed in the silicon substrate 16 and to form a circular or polygonal opening 138' at the location wherein a circular or polygonal opening 142 will be formed in the substrate 16.

Figure 16B:
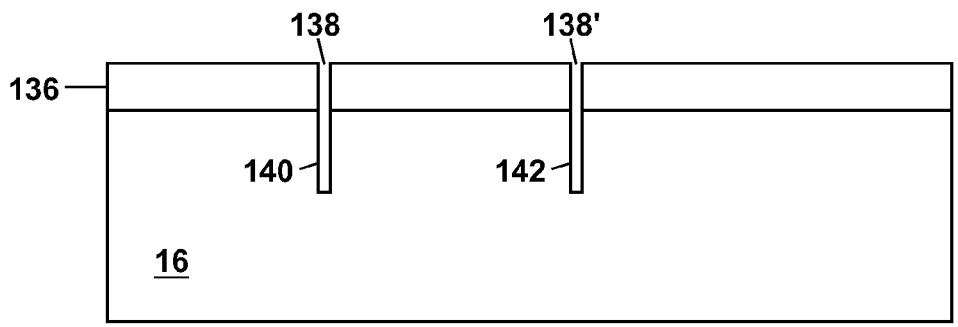

In FIG. 16B, the hard etch mask 136 is used to etch the trench 140 and the opening 142 down into the silicon substrate 16 to an etch depth of, for example, a few microns (e.g. 2-5 μm), with the trench 140 being, for example, 0.5 μm wide and with the opening 142 being, for example, 0.5 μm in diameter. Etching of the trench 140 and opening 142 can be performed using an RIE step. The hard etch mask 136 can then be removed using a selective wet etchant comprising HF.

Figure 16C:
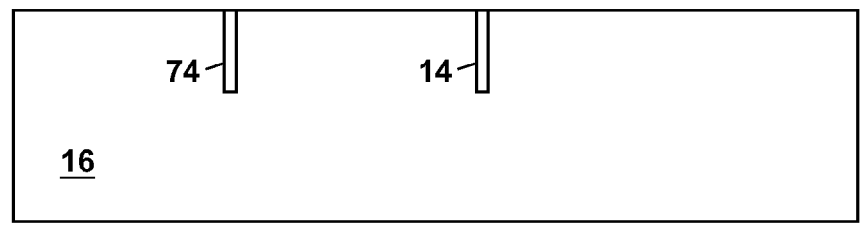

In FIG. 16C, the trench 140 and opening 142 can be filled in with silicon oxide, with the filled-in trench 140 being used to form a base 74 for an optical waveguide 20 which will be subsequently formed, and with the filled-in opening 142 being used to form a support post 14 for an optical resonator 12 of the thermal microphotonic sensor 10. The trench 140 and opening 142 can be filled in with silicon oxide by depositing the silicon oxide by CVD, or alternately by thermally oxidizing portions of the silicon substrate 16 which surround the trench 140 and opening 142.

Thermally oxidizing exposed portions of the silicon substrate 16 to fill in the trench 140 and opening 142 can be performed by heating the substrate 16 to about 1050° C. in an oxygen or steam ambient. This thermal oxidation step converts exposed portions of the silicon substrate 16, which form sidewalls and a bottom of both the trench 140 and opening 142, into silicon oxide which expands to fill in the trench 140 and opening 142 to form the base 74 and support post 14 as shown in FIG. 16C. It should be noted that the remainder of the silicon substrate 16 is protected from being oxidized by the thermal oxide and silicon nitride layers (not shown) which were initially formed over the silicon substrate 16 as previously described with reference to FIG. 16A. Any of the silicon oxide which expands above the trench 140 and opening 132 can be removed using a CMP step. The CMP step can also remove the thermal oxide and silicon nitride layers from a top side of the substrate 16.

A layer of silicon oxide (e.g. an undoped silica glass) having a layer thickness of, for example, 1 μm can be optionally deposited over the silicon substrate 16 by CVD and planarized by a CMP step. This can be useful, for example, when the silicon oxide does not completely fill in the trench 140.

Figure 16D:
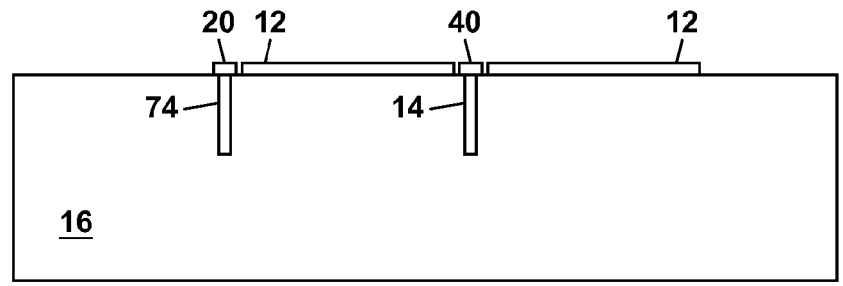

In FIG. 16D, another silicon nitride layer can be blanket deposited over the silicon substrate 16 by CVD to a layer thickness of, for example, 0.2-0.3 μm and then patterned using a photolithographically-defined etch mask (not shown) and an RIE step. The exact thickness of the silicon nitride layer can be adjusted, if needed, using another CMP step. Patterning this silicon nitride layer forms the optical waveguide 20, the optical resonator 12, a top 40 of the support post 14, and a plurality of tethers 18 which connect the optical resonator 12 to the top 40 of the support post 14.

After patterning the silicon nitride layer in FIG. 16D to form the various elements 12, 18, 20 and 40, a smoothing step can be performed to smooth the exposed surfaces of the optical waveguide 20 and optical resonator 12; and an annealing step can be performed to reduce the absorption of the light 22 in the waveguide 20 and resonator 12. The smoothing step has been previously described with reference to FIG. 3B; and the annealing step has been previously described with reference to FIG. 3C.

Figure 16E:
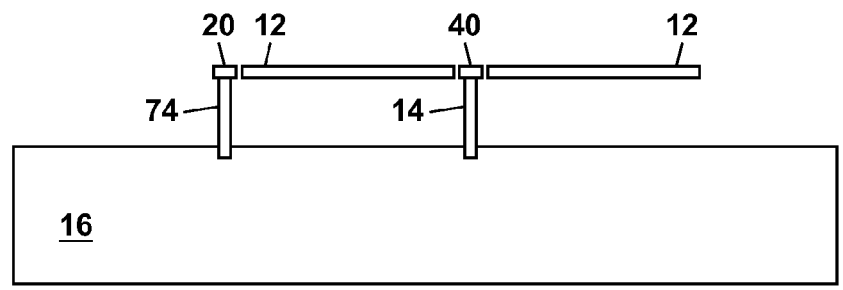

In FIG. 16E, to complete the thermal microphotonic sensor 10, the silicon substrate 16 can be partially removed by etching beneath the optical waveguide 20 and optical resonator 12. This can be done by etching the silicon substrate 16 to an etch depth which is less than the etch depth of the trench 140 and opening 142. This etching step leaves the base 74 and support post 14 firmly anchored into the silicon substrate 16 while elevating the optical waveguide 20 and optical resonator 12 above the substrate 16. This etching step can be performed using a selective etchant comprising, for example, KOH, EDP, TMAH or $XeF_2$ which etches away the silicon substrate material while not substantially chemically attacking the various elements of the sensor 10 which are formed of silicon oxide and silicon nitride.

To increase the absorption of incident infrared light 100, an infrared-absorbing coating 46 can be provided on the optical resonator 12 as described previously with reference to FIG. 5. Alternately, an infrared-absorbing plate 60 can be attached to the optical resonator 12. The use of an infrared-absorbing plate 60 is useful, for example, when the optical resonator 12 is formed with an open annular structure as shown in FIG. 8. The infrared-absorbing plate 60 can be added after forming the optical waveguide 20 and the optical resonator 12 as shown in FIG. 16D by providing a series of additional process steps which are described hereinafter with reference to FIGS. 17A-17C.

Figure 17A:
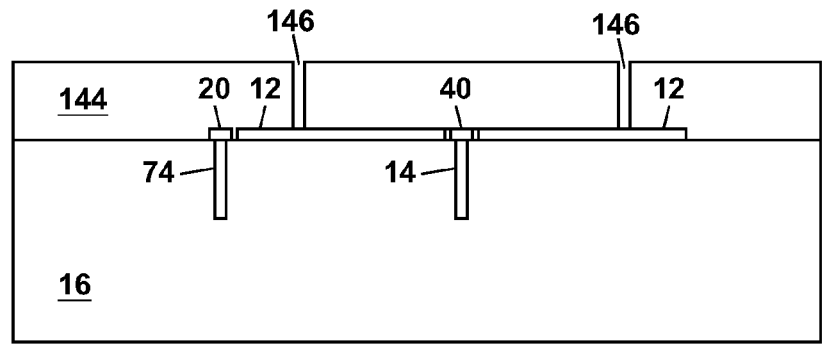
FIGS. 17A-17C show schematic cross-section views along the section line 4-4 in FIG. 15 to illustrate additional process steps which can be used to add an infrared-absorbing plate to the device of FIG. 15.

In FIG. 17A, a layer 144 of polysilicon can be blanket deposited over the substrate by CVD at a temperature of about 580° C. The polysilicon layer 144, which will be used as a sacrificial material and later removed with a selective etchant, can be, for example, 2 μm thick. The polysilicon layer 144 can be planarized after deposition using a CMP step. Openings 146 can then be etched through the polysilicon layer 144 at the locations where a plurality of legs 68 will be formed to support the infrared-absorbing plate 60 on the optical resonator 12. The openings 146 can be etched using an RIE step.

Figure 17B:
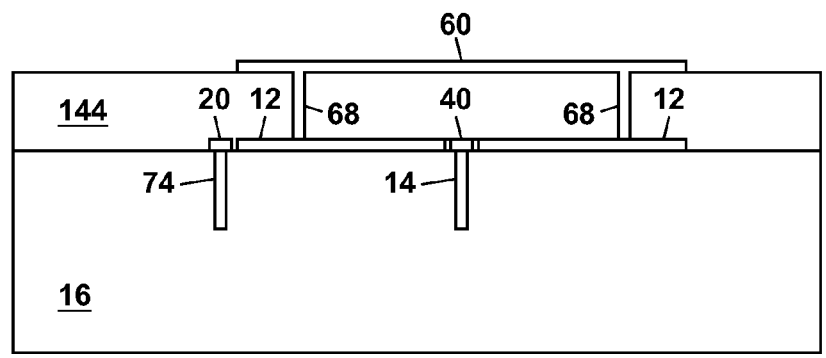
Figure 17C:
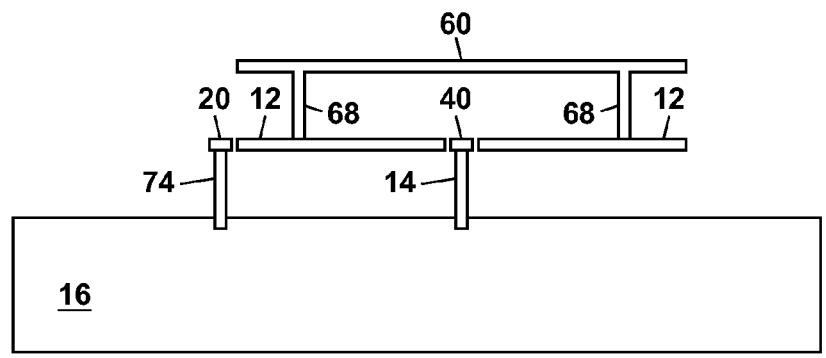

In FIG. 17B, a layer of silicon nitride about 0.2 μm thick, for example, can be blanket deposited over the polysilicon layer 144 and into the openings 146. This silicon nitride layer can then be patterned using a photolithographically-defined etch mask (not shown) and an RIE step to form the infrared-absorbing plate 60. A portion of this silicon nitride layer which fills in the openings 146 forms the legs 68 which attach the infrared-absorbing plate 60 to the optical resonator 12. These legs 68 thermally couple the infrared-absorbing plate 60 to the optical resonator 12 so that heat from the plate 60 due to incident infrared radiation 100 is conducted through the legs 68 into the optical resonator 12 to change the resonant frequency $f_0$ therein.

In FIG. 17C, the polysilicon layer 144 can be etched away using the selective etchant comprising KOH, EDP, TMAH or $XeF_2$. The etching step can be continued after completely removing the polysilicon layer 144 to etch the silicon substrate 16 down to an etch depth which is less than the etch depth of the trench 140 and opening 142. This leaves the optical waveguide 20 and optical resonator 12 elevated above the substrate 16 and firmly anchored thereto by the base 74 and support post 14, respectively, and completes the fabrication of the thermal microphotonic sensor 10.

Each of the examples of the thermal microphotonic sensor 10 described herein can be used to form individual sensors 10, or to form an one-dimensional (1-D) or two-dimensional (2-D) sensor array 90 comprising a plurality of sensors 10 on a common substrate 16. Such sensor arrays 90 have applications for infrared imaging without the need for cryogenic cooling.

Figure 10:
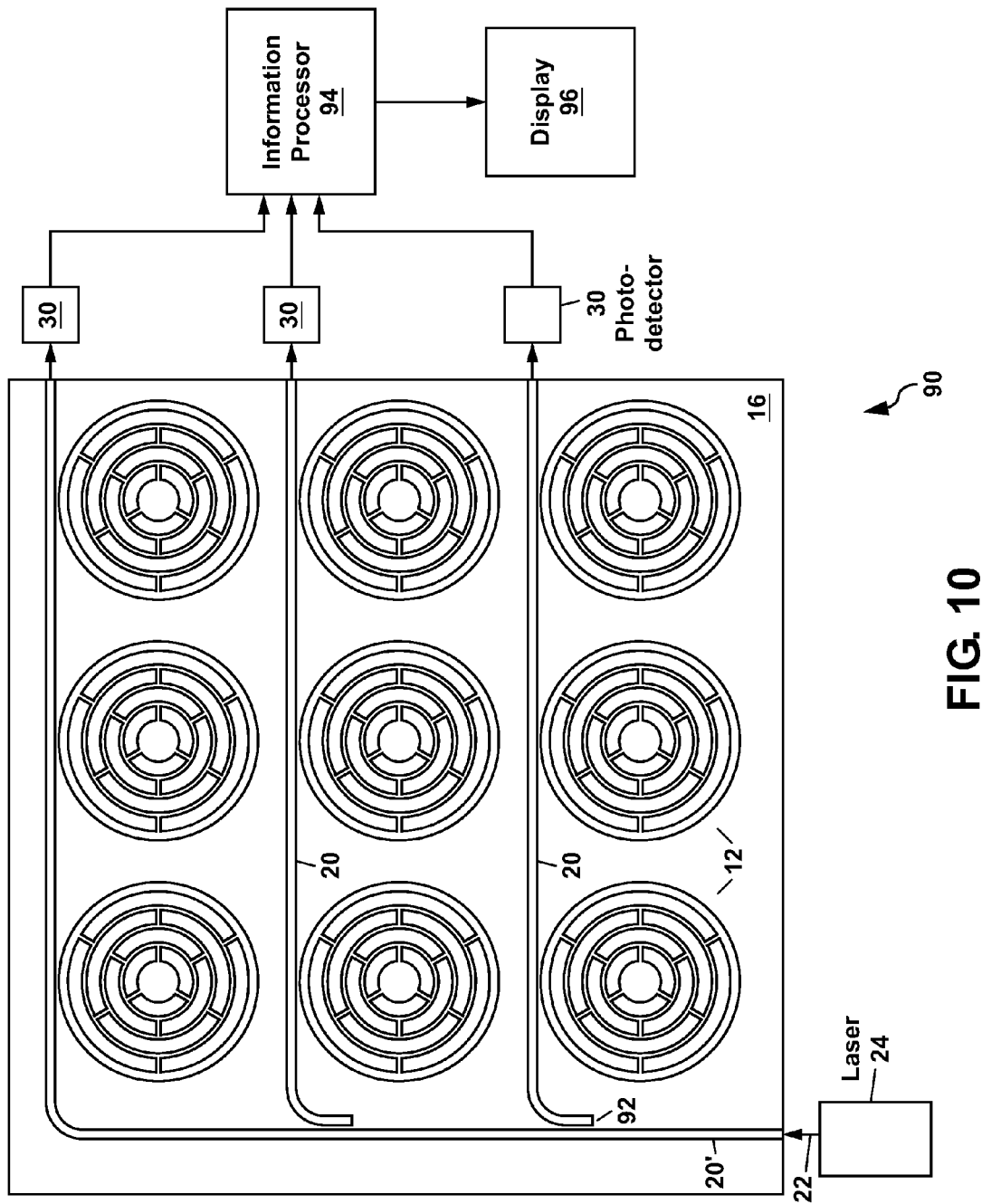
FIG. 10 shows a schematic diagram of a first example of a sensor array formed according to the present invention.

FIG. 10 shows a schematic plan view of an example of a sensor array 90 formed according to the present invention. In this example of the present invention, a plurality of optical resonators 12 are located on a common substrate 16, with the resonators 12 arranged in rows and columns to form the 2-D sensor array 90. Each row of the optical resonators 12 in FIG. 10 has a common optical waveguide 20. Although only a few resonators 12 and waveguides 20 are shown in FIG. 10, one skilled in the art will understand that there can be up to one million or more optical resonators 12 on the common substrate 16 when the sensor array 90 forms a focal plane array (FPA) for imaging infrared radiation 100. Each optical resonator 12 can define a pixel in the focal plane array 90, with each pixel being, for example, 5-20 μm in size. In the example of FIG. 10, an infrared absorber (e.g. an infrared-absorbing coating 46 or an infrared-absorbing plate 60) can be provided over each optical resonator 12 as previously described. The infrared absorber has been omitted from FIG. 10 for clarity.

In the example of FIG. 10, light 22 from a laser 24 can be coupled into an input optical waveguide 20' which can be routed for coupling to a top row of the optical resonators 12. A portion of the light 22 from the input optical waveguide 20' can also be split off using an evanescent waveguide coupler 92 to feed the waveguides 20 in each additional row of the optical resonators 12.

To individually address each optical resonator 12 in a particular row, each resonator 12 in that row can be formed with a different resonant frequency $f_1, f_2, \ldots f_n$ where n is the number of resonators 12 in each row. This can be done by making each resonator 12 with a slightly different size. The various sizes of the resonators 12 can be selected to provide a plurality of resonant frequencies which are equally spaced apart by a frequency interval of, for example, 0.1-10 GHz. The optical resonators 12 in each column of the sensor array 90 can have the same size thereby providing substantially the same resonant frequency for the resonators 12 in each column. Thus, the 3×3 sensor array 90 shown in FIG. 10 can have resonators 12 of three different sizes.

To form an image of a scene of interest using the sensor array 90, infrared light 100 from the scene of interest can be imaged onto the optical resonators 12 in the sensor array 90. This can be done using an optical train comprising one or more lenses or mirrors which have been omitted from FIG. 10 for clarity. A change in the resonant frequency of each resonator 12 due to heating of that optical resonator 12 by the infrared radiation 100 from the scene of interest can be determined to infer the intensity of the infrared radiation 100 to generate an infrared image of the scene of interest.

To read out the change in the resonant frequency of each resonator 12, each column of resonators can be read out separately. This can be done, for example, by tuning or stepping the frequency $f_L$ of the light 22 from the laser 24 to coincide with a predetermined reference point on the characteristic curve of each resonator 12 in a particular column of the array 90 and measuring the amount of the light 22 reaching the photodetectors 30. This will allow the shift of the resonant frequency of each resonator 12 in that column to be determined in a manner as previously described with reference to FIG. 2. The frequency $f_L$ of the light 22 from the laser 24 can then be tuned or stepped to coincide with the predetermined reference point on the characteristic curve of each resonator 12 in another column of the sensor array 90 and the measurement repeated for that column of resonators 12. In this way, each column of the optical resonators 12 can be read out with the infrared radiation intensity information being stored in an information processor 94 which can be a computer, a microcontroller, a digital signal processor, or a field programmable gate array. A reference characteristic curve for each resonator 12 in the sensor array 90 can also be measured from a scan of the frequency $f_L$ of the laser light 22 in the absence of any incident infrared radiation 100 and stored in the information processor 94 for reference in determining the frequency shift of each resonator 12 due to heating from the infrared radiation 100. The intensity information stored in the information processor 94 can be used to form the infrared image of the scene of interest which can be viewed on a display 96 (e.g. a computer screen).

In the sensor array 90 of FIG. 10, the intensity information for the infrared radiation 100 can also be determined by continuously tuning or stepping the frequency $f_L$ of the light 22 from the laser 24 to scan over the characteristic curve of each resonator 12 in the array 90. In this way, the characteristic curve for each resonator 12, which is shifted in frequency due to heating by the infrared radiation 100, can be measured from the light 22 exiting the optical waveguides 20 and 20' using the photodetectors 30. The characteristic curve for each resonator 12 can then be compared with the reference characteristic curve for that same resonator 12 to determine the exact frequency shift due to heating by the infrared radiation 100. This can be done for each resonator 12 in the sensor array 90 using the information processor 94. From the shift in the resonant frequency of each resonator 12 due to heating by the infrared radiation 100, the intensity of the infrared radiation 100 can be determined to construct the infrared image of the scene of interest.

Figure 11:
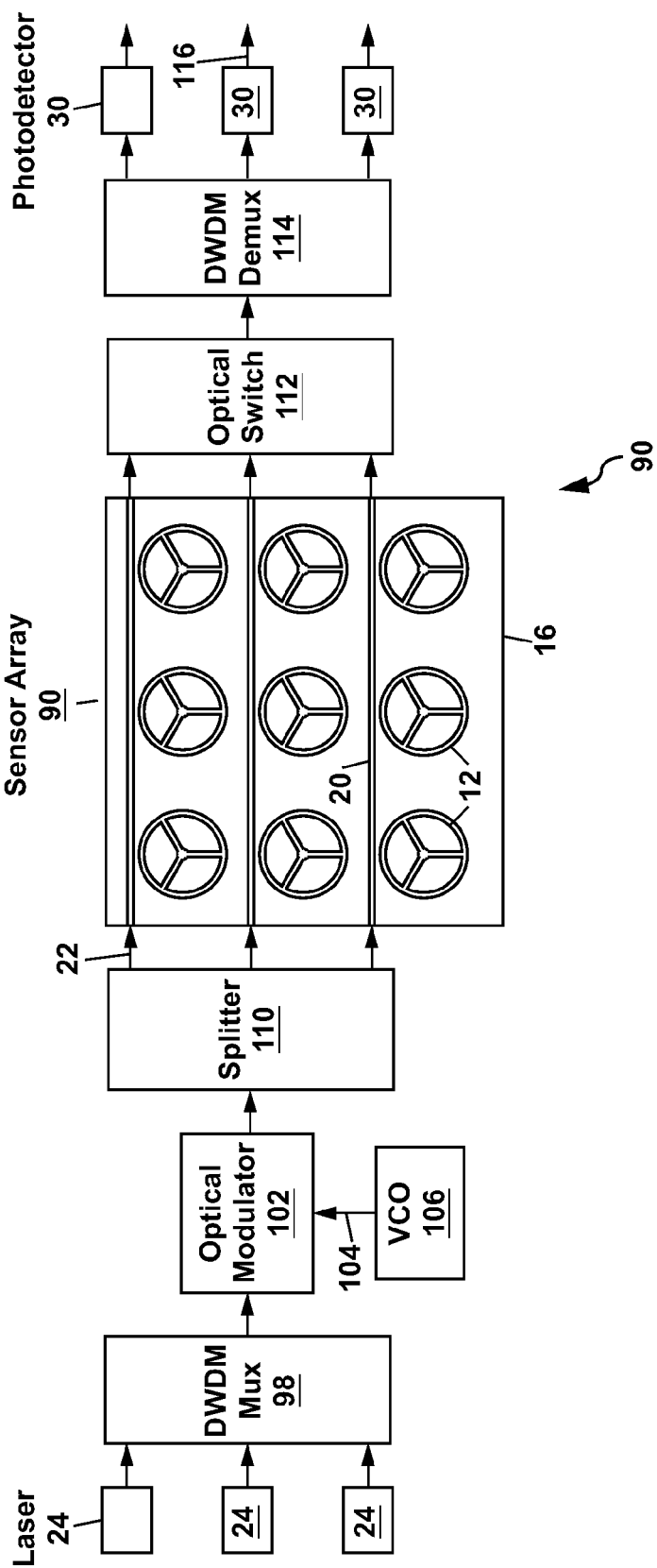
FIG. 11 shows a schematic diagram of a second example of a sensor array formed according to the present invention.

A wavelength division multiplexing (WDM) approach can also be used to read out the intensity information for the detected infrared radiation 100. In this case, which is schematically illustrated in FIG. 11, the light 22 comprises a plurality of different wavelengths which can be spaced apart in frequency. When the number of lasers 24 is the same as the number of resonators 12 in each row and column of the array 90 as shown in FIG. 11, then the different wavelengths of the light 22 from the lasers 24 can be spaced apart by about same amount (e.g. 10-50 GHz) as the different resonant frequencies $f_1, f_2, \ldots f_n$ of the resonators 12 in each row of the optical resonators 12.

In other embodiments of the present invention, when the number of resonators 12 in each row and column of the array 90 is much larger than the number of lasers 24, then a frequency spacing of adjacent resonators 12 in each row of the array 90 can be much smaller than the frequency spacing of the different wavelengths of the light 22 from the lasers 24. As an example, when each laser 24 is scanned to interrogate 10-100 resonators 12 in each row of the sensor array 90, then the resonators 12 can be spaced apart in frequency by 0.1-1 GHz. In this example, each column of the resonators 12 will generally be made with substantially the same resonant frequency.

The different wavelengths of the light 22 can each be provided by a separate fixed-wavelength single-frequency laser 24 (e.g. a DBR laser or a vertical-cavity surface-emitting laser operating at a wavelength near 1.5 μm) which can be individually packaged, or formed on a common substrate. The different wavelengths of the light 22 from the various lasers 24 can be combined in a conventional dense wavelength division multiplexer (DWDM Mux) 98, which is commonly used for fiber optic communications. The DWDM Mux 98 combines the light 22 from each laser 24 into a single beam of light 22 containing a plurality of different wavelengths as described above.

Figure 12:
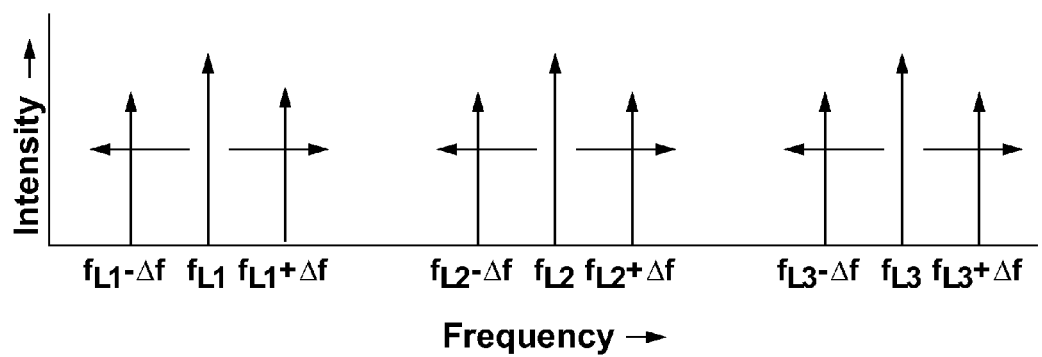
FIG. 12 shows a schematic representation of a frequency spectrum at an output of the optical modulator to illustrate the generation of a pair of tunable frequency sidebands which are generated on either side of a center frequency of the light from each laser due to modulation of the light from each laser.

To make each wavelength of the light 22 from the DWDM Mux 98 tunable over at least a portion of the characteristic curve for each resonator 12, an optical modulator 102 can be used. The light 22 can be fed into the optical modulator 102 using an optical fiber (not shown), with the optical modulator 102 being driven by a sinusoidal electrical input signal 104 from a voltage-controlled oscillator (VCO) 106. The VCO 106 can be programmed using an input voltage from the information processor 94, or from a signal generator. Alternately a digital frequency synthesizer which can be swept in frequency over time can be used to drive the optical modulator 102. In either case, the modulator 102 amplitude modulates the light 22 to generate a pair of frequency-tunable sidebands on either side of an optical carrier frequency of the light. This is schematically illustrated in FIG. 12 which shows the optical carrier frequencies $f_{L1}$, $f_{L2}$ and $f_{L3}$ from the three lasers 24 in FIG. 11. Also shown in FIG. 12 are the sidebands generated by the optical modulator 102 at the frequencies $f_{L1} \pm \Delta f$, $f_{L2} \pm \Delta f$ and $f_{L3} \pm \Delta f$ where $\Delta f$ is the frequency of the sinusoidal input signal 104. By changing the frequency $\Delta f$ from the VCO 106, the sidebands can all be simultaneously tuned up or down in frequency depending upon whether the frequency of the sinusoidal input signal 104 is added to or subtracted from the carrier frequencies $f_{L1}$, $f_{L2}$ and $f_{L3}$. The direction of tuning of each sideband frequency is indicated by the horizontal arrows in FIG. 12, with a range of tuning of each sideband frequency being, for example, 5-15 GHz away from one of the carrier frequencies $f_{L1}$, $f_{L2}$ and $f_{L3}$.

In the example of FIG. 11, one of the frequency-tunable sidebands from each laser 24 can be used to measure the frequency change (i.e. frequency shift) of each resonator 12 in a particular column of the resonators 12. The other sideband frequency and the optical carrier frequency can be selected so that they are not located near the resonant frequency of any of the resonators 12 and thus are not affected by any change in the resonant frequency of the resonators 12. Alternately, a narrowband optical filter 108 can be provided in the device 10 or array 90 to transmit only a single frequency-tunable sideband (see FIG. 13). In this case, the narrowband optical filter 108 can be centered about a frequency-tuning range of the sideband to be transmitted through the filter 108 and can have a bandpass sufficiently wide so as to not appreciably attenuate the sideband over the frequency-tuning range. At the same time, the bandpass of the narrowband optical filter 108 can be sufficiently narrow to block the transmission of the other frequency-tunable sideband and the optical carrier frequency. In other embodiments of the present invention, the two frequency-tunable sidebands associated with each carrier frequency $f_{L1}$, $f_{L2}$ and $f_{L3}$ can be used to measure the frequency change of two different resonators 12 in the same row of the optical resonators 12.

Each row of the resonators 12 in FIG. 11 can be separately interrogated with the multi-frequency tunable light 22. This can be done by providing a splitter 110 (e.g. a conventional fiber optic splitter, or a series of beam-splitting mirrors) to divide the beam of light 22 from the modulator 102 into multiple beams all having about the same intensity. Each of these multiple beams of the light 22 can be directed into a separate optical waveguide 20 as shown in FIG. 11.

The light 22, after being transmitted through the various optical waveguides 20, is directed into an optical switch 112 which can be used to select the light 22 from each optical waveguide 20 in turn for further processing and detection. As the light 22 from a particular optical waveguide 20 is selected by the optical switch 112, this light 22 is directed into a dense wavelength division demultiplexer (DWDM Demux) 114 which spatially separates out the various sideband frequencies used to measure the frequency shifts of the different resonators 12 in a particular row and directs each sideband frequency of the light 22 to a different photodetector 30 for detection. An electrical output signal 116 is generated by each photodetector 30. This electrical output signal 116, which is proportional to an intensity of the infrared radiation 100 sensed by the optical resonators 12 via heating thereof, can then be directed to an information processor 94 (see FIG. 10), and therefrom to an optional display 96.

Electrical amplifiers, which are not shown in FIG. 11, can also be optionally provided in the sensor array 90 of FIG. 11 to amplify the electrical output signal 116 from each photodetector 30. Narrowband optical filters 108 can also be optionally provided in the sensor array 90 of FIG. 11. The narrowband optical filters 108 can be used as previously described to transmit only one of the frequency-tunable sidebands associated with each carrier frequency, and to remove the other frequency-tunable sideband and each optical carrier frequency.

Another way of measuring the change in frequency of each optical resonator 12 in response to heating by the infrared radiation 100 is to linearly vary the frequency of the sinusoidal input signal 104 to the optical modulator 102 at a known rate, and then measure the time when the frequency-tunable sideband of the light 22 is swept across a particular reference point on each side of the characteristic curve of each optical resonator 12. This can be done initially without any infrared radiation 100 incident on the optical resonators 12 to establish values of the timing for scanning across the reference points on each side of an unshifted characteristic curve centered about the resonant frequency $f_0$ of each unperturbed resonator 12. These timing values can be stored in the information processor 94. The timing measurement can then be repeated with the infrared radiation 100 heating the optical resonators 12 to shift the resonant frequencies therein. A difference between the timing values for each optical resonator 12 with and without the incident infrared radiation 100 can then be used to calculate the frequency shift in each optical resonator 12 and thereby determine the intensity of the infrared radiation 100 responsible for heating that resonator 12.

Figure 13:
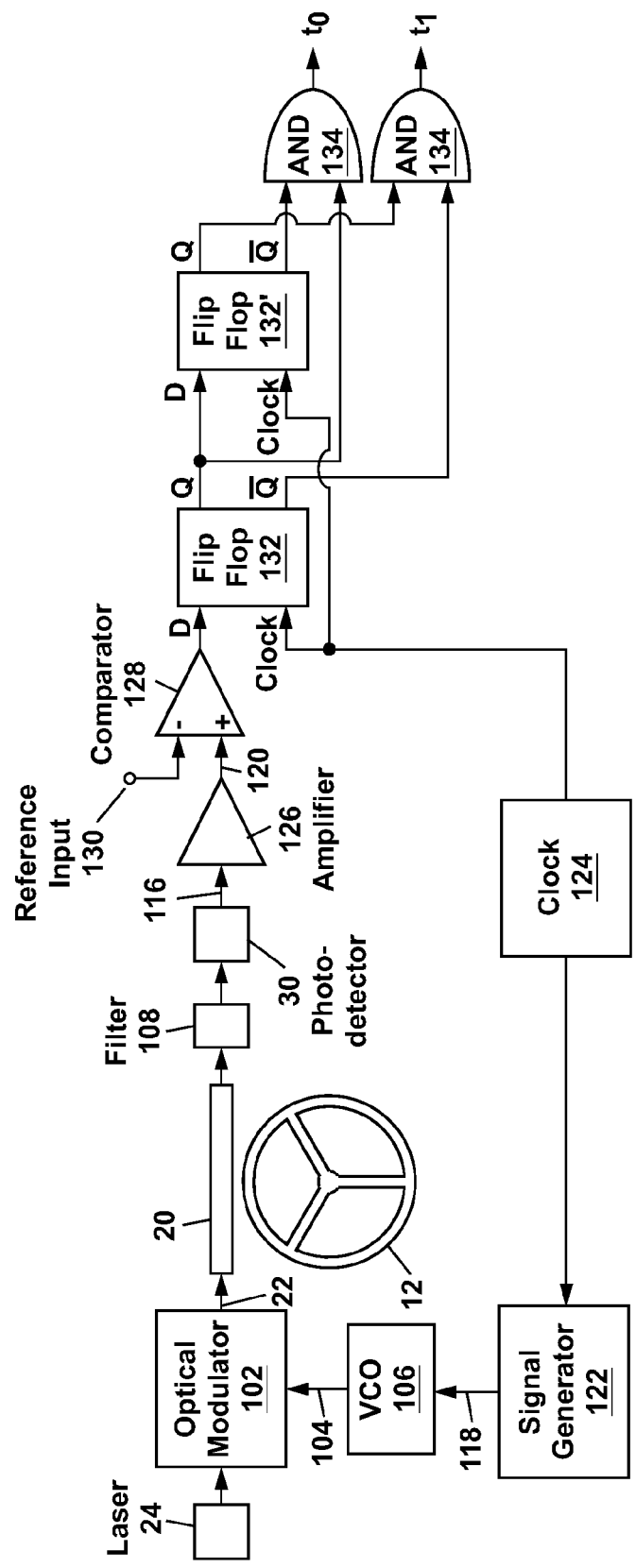
FIG. 13 shows a schematic diagram of a third example of a sensor array formed according to the present invention.

A circuit for implementing this timing measurement for a single optical resonator 12 using a single laser 24 and a single photodetector 30 is schematically illustrated in FIG. 13. Those skilled in the art will understand that the circuit presented herein with reference to FIG. 13 can be replicated for each photodetector 30 in the sensor array 90 of FIG. 11.

In FIG. 13, the light 22 from the laser 24 is modulated using the optical modulator 102 which is driven by the VCO 106. To provide a linearly-increasing input voltage 118 to the VCO 106 and thereby provide a linear scan rate for tuning of the sideband frequencies of the light 22 generated by the modulator 102, a signal generator 122 can be used with an input from a clock 124.

Figure 14:
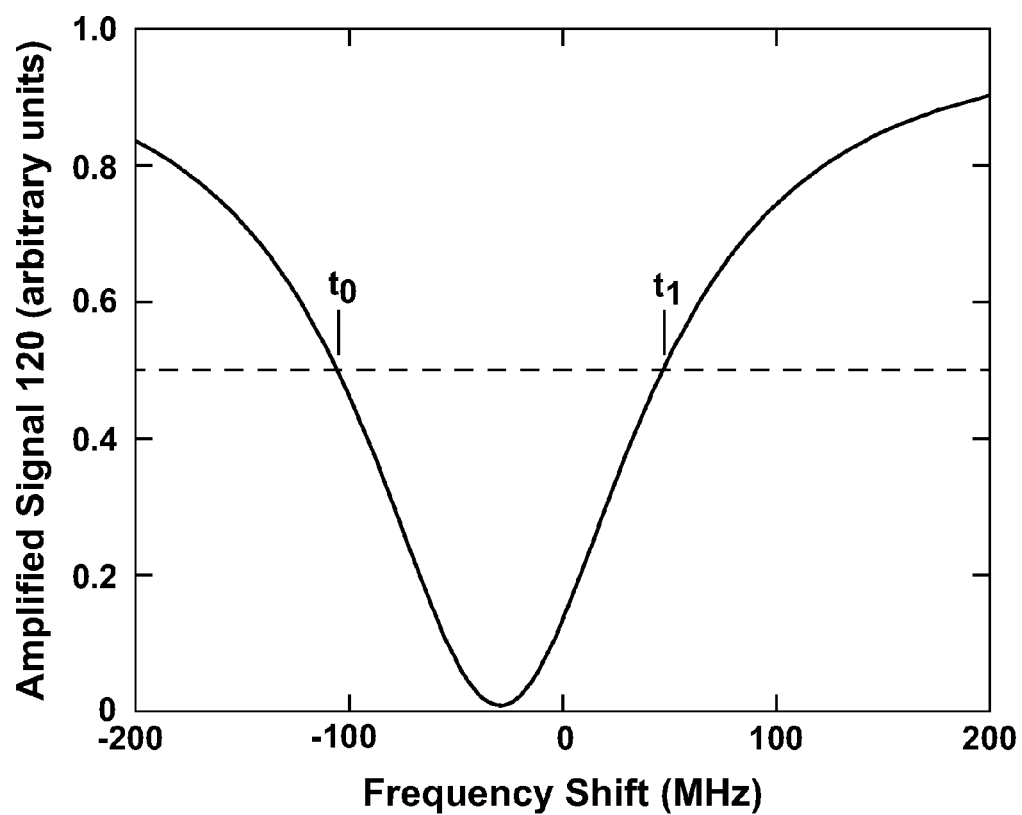
FIG. 14 shows the amplified signal in the sensor array of FIG. 13 as the sideband frequency of the light is scanned across the characteristic curve of a heated resonator to illustrate how the frequency shift of the resonator can be determined from the times $t_0$ and $t_1$ when the characteristic curve intersects a reference point (indicated by the horizontal dashed line).

After the light 22 has passed through the optical waveguide 20, a narrowband optical filter 108 can be used to transmit only one sideband frequency of the light 22 to the photodetector 30 and to filter out the other sideband frequency and the optical carrier frequency. The electrical output signal 116 from the photodetector 30 can be amplified with an amplifier 126 to produce an amplified signal 120 as shown in FIG. 13. The amplified signal 120 can then be input into a comparator 128 where the amplified signal 120 is compared to a reference input voltage 130. The reference input voltage 130 has a dc voltage level which defines a reference point on each side of the characteristic curve for the resonator 12. This reference point can be, for example, 0.1-0.5 of a peak voltage of the amplified signal 120. This is illustrated in FIG. 14 where the reference point is defined by the intersection of the horizontal dashed line, which represents the reference input voltage 130, with the characteristic curve of the resonator 12. The characteristic curve of the resonator 12 in FIG. 14 shows the variation in the amplified signal 120 as the sideband frequency of the light 22 is tuned over a range of 400 MHz.

The comparator 128 provides an output signal which will undergo a change in state whenever the difference between the amplified signal 120 and the reference input 130 changes sign. As shown in FIG. 14, this will occur twice—at a time designated as $t_0$, and again at a time designated as $t_1$. A current state and a previous state of the output signal of the comparator 128 can be sensed using a pair of sequential D-type flip-flops 132 and 132' which are clocked with a signal provided by the clock 124. At any point in time, a current bit representing the current state of the comparator 128 can be stored in the first flip-flop 132, and a previous bit representing the previous state of the comparator 128 can be stored in the second flip-flop 132'. A Q output from each flip-flop can then be combined with a Q-bar output from the other flip-flop in an AND gate 134 as shown in FIG. 13. This provides a timing pulse from one of the AND gates 134 at the time $t_0$, and another timing pulse from the other AND gate 134 at the time $t_1$. The exact timing of the two timing pulses can be compared with the timing pulses obtained for the same resonator 12 in the absence of the infrared radiation 100 and with the linear scan rate of the sideband frequencies of the light 22 to determine the exact frequency shift due to heating of the resonator 12 by the infrared radiation 100. The circuit of FIG. 13 thus converts the measurement of the frequency shift in the characteristic curve of the resonator 12 to a timing measurement. To improve the accuracy of this timing measurement, the timing pulses at $t_0$ and $t_1$ can be averaged. Processing of the timing measurement information can be performed in the information processor 94 and compared to similar timing measurements for the resonator 12 without any heating by the infrared radiation 100.

The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A method for fabricating a thermal microphotonic sensor for detecting infrared radiation, comprising the steps of:
   providing a silicon substrate;
   etching at least one opening and at least one trench in the silicon substrate to a first etch depth, with each opening being located where a support post for an optical resonator will be subsequently formed, and with each trench being located where a base for an optical waveguide will be subsequently formed;
   filling in each opening and each trench with silicon oxide;
   depositing a layer of silicon nitride over the silicon substrate, and patterning the layer of silicon nitride to form each optical resonator and each optical waveguide; and
   etching the silicon substrate beneath each optical resonator and beneath each optical waveguide to a second etch depth which is less than or equal to the first etch depth and thereby elevating each optical resonator and each optical waveguide above the silicon substrate, with each optical resonator being elevated upon the support post, and with each optical waveguide being elevated upon the base which is located therebeneath.

2. The method of claim 1 wherein the step of etching the at least one opening and the at least one trench in the silicon substrate comprises reactive ion etching each opening and each trench in the silicon substrate.

3. The method of claim 1 wherein the step of filling in each opening and each trench with silicon oxide comprises thermally oxidizing portions of the silicon substrate surrounding each opening and each trench and thereby converting these portions of the silicon substrate into the silicon oxide which expands to fill in each opening and each trench.

4. The method of claim 3 further comprising a chemical-mechanical polishing step for removing any of the silicon oxide which expands above each opening and each trench prior to the step of depositing the layer of silicon nitride over the silicon substrate.

5. The method of claim 1 wherein the step of depositing the layer of silicon nitride over the silicon substrate comprises depositing the layer of silicon nitride by chemical vapor deposition.

6. The method of claim 1 wherein the step of depositing the layer of silicon nitride over the silicon substrate comprises depositing the layer of silicon nitride to a thickness in the range of 0.2 to 0.3 microns.

7. The method of claim 1 further comprising the step of chemical-mechanically polishing the layer of silicon nitride prior to patterning the layer of silicon nitride to form each optical resonator and each optical waveguide.

8. The method of claim 1 wherein the step of patterning the layer of silicon nitride to form each optical resonator and each optical waveguide comprises the steps of masking the layer of silicon nitride with a photolithographically-defined etch mask and reactive ion etching portions of the layer of silicon nitride which are not protected from etching by the photolithographically-defined etch mask.

9. The method of claim 1 wherein the step of etching the silicon substrate comprises etching the silicon substrate with a selective etchant which etches the silicon substrate to the second etch depth without substantially chemically attacking the silicon oxide or the layer of silicon nitride.

10. The method of claim 9 wherein the selective etchant comprises a selective wet etchant selected from the group consisting of potassium hydroxide (KOH), ethylene diamine-pyrocatechol (EDP) and tetramethyl ammonium hydroxide (TMAH).

11. The method of claim 9 wherein the selective etchant comprises xenon difluoride ($XeF_2$).

12. The method of claim 1 wherein the step of patterning the layer of silicon nitride forms a plurality of tethers to connect each optical resonator to the support post for that optical resonator.

13. The method of claim 1 further comprising the step of depositing an infrared-absorbing coating on each optical resonator.

14. The method of claim 1 further comprising the steps of:
   depositing a layer of polycrystalline silicon over the silicon substrate after the step of patterning the layer of silicon nitride to form each optical resonator and each optical waveguide;
   etching the layer of polycrystalline silicon to provide a plurality of openings down to the optical resonator at locations where a plurality of legs will be subsequently formed;
   depositing another layer of silicon nitride over the layer of polycrystalline silicon and in the plurality of openings down to the optical resonator, with the layer of silicon nitride in the plurality of openings forming the plurality of legs;
   patterning the layer of silicon nitride over the layer of polycrystalline silicon and thereby forming an infrared-absorbing plate which is thermally coupled to the optical resonator by the plurality of legs; and etching away the layer of polycrystalline silicon prior to the step of etching the silicon substrate.

15. A method for fabricating a thermal microphotonic sensor for detecting infrared radiation, comprising the steps of:

providing a silicon substrate;

etching at least one opening and at least one trench in the silicon substrate to a first etch depth, with each opening being located where a support post for an optical resonator will be subsequently formed, and with each trench being located where a base for an optical waveguide will be subsequently formed;

filling in each opening and each trench with silicon oxide which is formed from the silicon substrate by thermally oxidizing portions of the silicon substrate surrounding each opening and each trench;

chemically-mechanically polishing the silicon substrate and thereby removing any of the silicon oxide which extends above the silicon substrate;

depositing a layer of silicon nitride over the silicon substrate;

reactive ion etching the layer of silicon nitride to form each optical resonator and each optical waveguide; and selectively etching the silicon substrate down to a second etch depth which is less than or equal to the first etch depth and thereby elevating each optical resonator and each optical waveguide above the silicon substrate.

16. The method of claim 15 further comprising the step of chemically-mechanically polishing the layer of silicon nitride prior to reactive ion etching the layer of silicon nitride to form each optical resonator and each optical waveguide.

17. The method of claim 15 wherein the step of reactive ion etching the layer of silicon nitride forms a plurality of tethers to connect each optical resonator to the support post for that optical resonator.

18. The method of claim 15 wherein the step of selectively etching the silicon substrate comprises selectively etching the silicon substrate using a selective etchant selected from the group consisting of potassium hydroxide (KOH), ethylene diamine-pyrocatechol (EDP), tetramethyl ammonium hydroxide (TMAH) and xenon difluoride ($XeF_2$).

19. The method of claim 15 further comprising the step of depositing an infrared-absorbing coating on each optical resonator.

20. The method of claim 15 further comprising the steps of:

depositing a layer of polycrystalline silicon over the silicon substrate after the step of reactive ion etching the layer of silicon nitride to form each optical resonator and each optical waveguide;

reactive ion etching the layer of polycrystalline silicon to provide a plurality of openings down to the optical resonator at locations where a plurality of legs will be subsequently formed;

depositing another layer of silicon nitride on the layer of polycrystalline silicon and in the plurality of openings down to the optical resonator, with the layer of silicon nitride in the plurality of openings forming the plurality of legs;

reactive ion etching the layer of silicon nitride on the layer of polycrystalline silicon and thereby forming an infrared-absorbing plate which is thermally coupled through the plurality of legs to the optical resonator; and selectively etching away the layer of polycrystalline silicon prior to the step of selectively etching the silicon substrate.

* * * * *